(12) United States Patent
Hurtig et al.

(10) Patent No.: US 11,017,643 B2
(45) Date of Patent: *May 25, 2021

(54) METHODS AND SYSTEMS FOR AUGMENTATIVE AND ALTERNATIVE COMMUNICATION

(71) Applicant: UNIVERSITY OF IOWA RESEARCH FOUNDATION, Iowa City, IA (US)

(72) Inventors: Richard Hurtig, Philadelphia, PA (US); Benjamin Berkowitz, Iowa City, IA (US); Blake Earl Martinson, Charlotte, NC (US); Zihan Zhu, Iowa City, IA (US); Richard Rives Bird, Coralville, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/410,831

(22) Filed: May 13, 2019

(65) Prior Publication Data

US 2019/0272718 A1    Sep. 5, 2019

Related U.S. Application Data

(63) Continuation of application No. 15/409,004, filed on Jan. 18, 2017, now Pat. No. 10,339,768, which is a
(Continued)

(51) Int. Cl.
*G08B 5/22* (2006.01)
*G06F 3/01* (2006.01)
*G16H 40/63* (2018.01)
(Continued)

(52) U.S. Cl.
CPC ............. *G08B 5/222* (2013.01); *A61F 4/00* (2013.01); *G06F 3/011* (2013.01); *G06F 3/013* (2013.01); *G06F 3/017* (2013.01); *G06F 3/0487* (2013.01); *G06F 3/04883* (2013.01); *G06F 3/16* (2013.01); *G06F 3/167* (2013.01); *G16H 40/63* (2018.01); *H03K 17/962* (2013.01); *G06F 3/041* (2013.01); *G06F 2203/038* (2013.01); *G06F 2203/0381* (2013.01); *H03K 2217/96003* (2013.01)

(58) Field of Classification Search
CPC ........... G08B 5/222; G16H 40/63; A61F 4/00; G06F 3/011; G06F 3/013; G06F 3/017; G06F 3/0418; G06F 3/0487; G06F 3/04883; G06F 3/16; G06F 3/167; G06F 3/041; G06F 2203/038; G06F 2203/0381; G06F 19/3406; H03K 17/962; H03K 2217/96003
USPC ..................................... 340/4.1–4.14; 341/21
See application file for complete search history.

(56) References Cited

U.S. PATENT DOCUMENTS 4,081,623 A * 3/1978 Vogeley .................... A61F 4/00
250/221
5,335,313 A * 8/1994 Douglas ................. A61G 7/018
379/355.01

(Continued)

*Primary Examiner* — Edwin C Holloway, III
(74) *Attorney, Agent, or Firm* — Ballard Spahr LLP

(57) ABSTRACT

Methods and systems for augmentative and alternative communication are disclosed. An example method can comprise receiving a candidate input, classifying the candidate input as an intentional input, and generating a signal in response to the intentional input.

20 Claims, 22 Drawing Sheets

Related U.S. Application Data continuation of application No. 14/993,889, filed on Jan. 12, 2016, now Pat. No. 9,595,171, which is a continuation-in-part of application No. PCT/US2014/046356, filed on Jul. 11, 2014.

(60) Provisional application No. 61/845,673, filed on Jul. 12, 2013.

(51) Int. Cl.
*G06F 3/0487* (2013.01)
*H03K 17/96* (2006.01)
*G06F 3/16* (2006.01)
*G06F 3/0488* (2013.01)
*A61F 4/00* (2006.01)
*G06F 3/041* (2006.01)

(56) References Cited

U.S. PATENT DOCUMENTS

| | | | |
|---|---|---|---|
| 5,360,971 A * | 11/1994 | Kaufman | A61B 3/113 250/221 |
| 5,493,618 A * | 2/1996 | Stevens | G08C 23/02 381/110 |
| 5,600,311 A * | 2/1997 | Rice | A61F 4/00 340/4.11 |
| 6,636,763 B1 * | 10/2003 | Junker | G06F 3/013 340/4.11 |
| 9,595,171 B2 * | 3/2017 | Hurtig | G06F 3/0418 |
| 10,339,768 B2 * | 7/2019 | Hurtig | G06F 3/017 |
| 2009/0058663 A1 * | 3/2009 | Joshi | G01D 11/24 340/584 |

* cited by examiner

METHODS AND SYSTEMS FOR AUGMENTATIVE AND ALTERNATIVE COMMUNICATION

CROSS REFERENCE TO RELATED PATENT APPLICATIONS

This application is a Continuation of U.S. application Ser. No. 15/409,004, filed Jan. 18, 2017, which is a Continuation of U.S. application Ser. No. 14/993,889, filed Jan. 12, 2016, and issued as U.S. Pat. No. 9,595,171, on Mar. 14, 2017, which claims priority to International Application No. PCT/US2014/046356 with an international filing date of Jul. 11, 2014, which claims priority to U.S. Provisional Application No. 61/845,673, filed Jul. 12, 2013, all of which are herein incorporated by reference in their entireties.

BACKGROUND

Current hospital accreditation standards mandate that all patients be provided with the means to summon the assistance of caregivers (e.g. nurse call). Many critical care patients are too weak to activate standard or alternative nurse call switches that are available at most facilities. Mechanical ventilation further limits patients to use voice to summon or communicate with caregivers. For many patients in intensive care and long term acute care settings, there are no existing communication methods that can transduce the minimal intentional gestures that these patients are capable of making. These and other shortcomings are addressed in the present disclosure.

SUMMARY

It is to be understood that both the following general description and the following detailed description are exemplary and explanatory only and are not restrictive, as claimed. Provided are methods and systems for augmentative and alternative communication. An example method can comprise receiving a candidate input, classifying the candidate input as an intentional input, and generating a signal in response to the intentional input.

Another example method can comprise receiving a candidate input. The candidate input can be classified as an intentional input. One or more devices associated with the intentional input can be determined. A signal can be generated to control the one or more devices associated with the intentional input.

An example apparatus can comprise an input interface, an output interface, a memory and a processor coupled to the input interface, the output interface, and the memory. The input interface can be configured for receiving a candidate input from one or more sensors. The output interface can be configured for transmitting a signal to a controlled device. The memory can be configured for storing a filter. The processor can be configured to classify the candidate input received by the input interface by applying the filter stored in the memory, and providing the signal to the output interface for transmission to the controlled device.

Additional advantages will be set forth in part in the description which follows or may be learned by practice. The advantages will be realized and attained by means of the elements and combinations particularly pointed out in the appended claims.

BRIEF DESCRIPTION OF THE DRAWINGS

The accompanying drawings, which are incorporated in and constitute a part of this specification, illustrate embodiments and together with the description, serve to explain the principles of the methods and systems.

DETAILED DESCRIPTION

Figure 1:
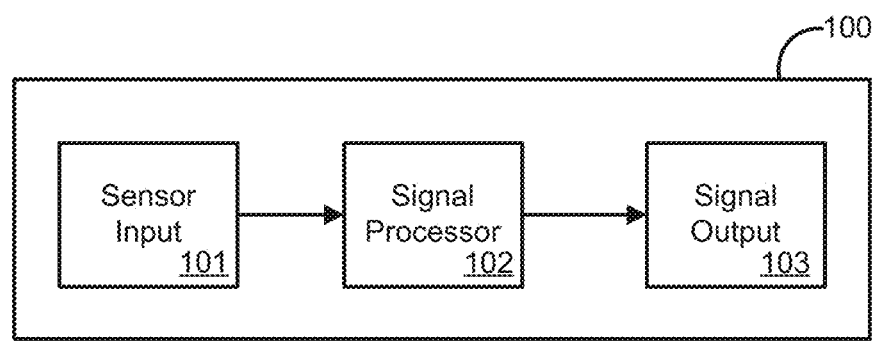
FIG. 1 is an exemplary apparatus capable of performing the methods disclosed.

Before the present methods and systems are disclosed and described, it is to be understood that the methods and systems are not limited to specific methods, specific components, or to particular implementations. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present methods and systems may be understood more readily by reference to the following detailed description of preferred embodiments and the examples included therein and to the Figures and their previous and following description.

As will be appreciated by one skilled in the art, the methods and systems may take the form of an entirely hardware embodiment, an entirely software embodiment, or an embodiment combining software and hardware aspects. Furthermore, the methods and systems may take the form of a computer program product on a computer-readable storage medium having computer-readable program instructions (e.g., computer software) embodied in the storage medium. More particularly, the present methods and systems may take the form of web-implemented computer software. Any suitable computer-readable storage medium may be utilized including hard disks, CD-ROMs, optical storage devices, or magnetic storage devices.

Embodiments of the methods and systems are described below with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

Provided are methods and systems for augmentative and alternative communication. The disclosed methods and systems can process complex signals embedded in complex noise in order to use the signals to allow a patient or user to control one or more devices in their environment, e.g. activating nurse call or patient controlled pain pumps, speech generating communication devices, and the like. In an aspect, the disclosed methods and systems can improve signal interpretation for a diverse set of input devices (e.g., acoustic, pressure, proximity and reflectance) used for augmentative and alternative communication devices for a variety of users. An exemplary application can include patients in a hospital setting who are paralyzed or severely incapacitated. The methods and systems provided can eliminate background noise (e.g., from hospital equipment) and other environmental sources as well as non-communication initiated movements from the patient (for example, normal eye blinks). The disclosed methods and systems can distinguish the intentional gesture from the ambient noise received from the environment or from non-intentional tremor in the patient's gestures. In an aspect, the methods and systems disclosed can be used in a hospital environment to enable intubated and otherwise disabled patients to communicate with caregivers. The methods and systems can be used by other care facilities such as outpatient facilities and elderly care facilities.

In an aspect, the disclosed methods and systems can comprise signal processing that can analyze the kinematics of intentional gestures that can be transduced and serve as inputs. For example, the methods can comprise intentional input detection regardless of the input modality (e.g., audio, tactile, pressure, IR reflectance). For example, rather than responding each time a user touches a switch plate, a signal processing switch can effectively filter out the unintentional touches and only respond to an intentional touch. This can be achieved by identifying the intentional gesture based on characteristics of the intentional gesture in the frequency domain, the time domain, or both.

An exemplary apparatus 100, shown in FIG. 1, can comprise one or more sensor inputs 101 for sensors such as microphones, pressure bulbs, pressure transducers, and the like. These sensor inputs can be processed by a signal processor 102 to classify a specific stimulus as intentional, as distinguished from noise and unintentional stimuli. The apparatus can be configured to a signal output 103 to control a device, which can be activated by the intentional stimulus and an optional visual output which can display to the user a menu of instructions and options. As an example, a controlled device can comprise one or more of a nurse call switch, a computer, a television, a telephone, a medical device, an application (e.g., iPad applications), a speech generating device, and the like. In an aspect, the signal output 103 can be used to invoke keyboard commands for communication or controlling other mechanical or computerized outputs. In an aspect, any type of sensor and any type of output can be utilized.

In an aspect, the methods and systems can be configured to operate in conjunction with a touch switch. A common problem with signals from switches activated by touch (either mechanical or capacitance/proximity detector switches) is that in order to respond to gestures that generate minimal displacement and force, the sensors are so sensitive that they are often activated unintentionally by tremors that often accompany the intentional gesture. A characteristic of the tremor can be determined and processed to generate a filter. For example, a tremor can generate a signal from about 4 Hz to about 12 Hz, for example a 4 Hz, 5 Hz, 6 Hz, 7 Hz, 8 Hz, 9 Hz, 10 Hz, 11 Hz, and/or 12 Hz signal. The disclosed methods and systems can comprise applying a low pass filter to the signal received from a touch switch to account for the tremors. In an aspect, an intentional tremor can have a frequency of below about 5 Hz. The methods and systems can then respond to the underlying intentional gesture and not to any higher frequency signals received from the transducer that are the consequence of the tremor in the gesture.

In an aspect, the methods and systems can be configured to operate in conjunction with a pressure sensor. For patients who cannot generate either the force or displacement necessary to activate touch switches, a pressure sensor can be used. Pressure sensors can be implemented as "sip-and-puff switches" used by individuals who are quadriplegic or paraplegic. These switches require that the user generate adequate changes in oral pressure. For individuals who cannot generate the oral pressure needed to activate the "sip-and-puff switches," one can use a closed silastic bulb that only requires a lip closure or a biting gesture. Such a bulb can be positioned just to the side of the user's mouth and a small lip gesture can allow the user to grasp the bulb and thus generate a positive pressure change.

However, many intubated or trached patients, who are also unable to move, prefer to keep the silastic bulb in their mouths. A consequence of this is that the small inadvertent movements of the lips and tongue that are not associated with the intentional gesture are also generating pressure changes. The disclosed methods and systems can determine a characteristic of the inadvertent movements and generate a filter to account for the inadvertent movements. For example, the methods and systems can analyze a time course of lip gestures and magnitude of the pressure changes associated with an intentional gesture, thereby generating a filter that can discriminate between intentional and unintentional inputs based on particular pressure changes over a particular time interval.

In an aspect, the methods and systems can be configured to operate in conjunction with an infrared sensor, such as an infrared reflectance switch. For many spinal cord injury patients as well as patients with locked-in-syndrome, the only motor gestures that they can reliably generate involve eyelid control. An eye-blink switch can be utilized to detect changes in reflected infrared light that are a consequence of eyelid movements. A problem is that existing eye-blink switches have difficulty distinguishing the reflectance changes associated with an intentional blink gesture from those associated with unintentional blink gestures, such as natural blinks or slower lid movements associated with either gaze shifts or lid dropping associated with drowsiness. The disclosed methods and systems can determine a characteristic of the intentional movements and generate a filter to account for the unintentional movements. In an aspect, the disclosed methods and systems can use kinematic analysis of eyelid movements for blink detection which is not responsive to the rapid reversal of reflectance associated with a natural blink, nor to the slower reflectance changes associated with slower involuntary lid movements. The methods and systems can set temporal cutoffs that only respond to the reflectance changes associated with the intermediate temporal duration of the intentional blink/wink.

In an aspect, the methods and systems can be configured to operate in conjunction with an audio sensor. For individuals who are able to generate sound, a Schmidt-trigger circuit (e.g., Voice Switch, Clapper switch) can be used. A problem with such a switch is that the switch can be triggered by a wide range of sounds and are not responsive to just a particular sound. As a result, there are many false positives and false negatives that result from variations in the audio signal intensity. In a hospital environment, many patients attempt to get staff attention by generating "small mouth" sounds. These sounds are made by small tongue movements or by popping of the lips. These are acoustically very low-amplitude signals that are often buried in the ambient noise. Ambient noise can include, for example, noise generated by equipment in the intensive care setting or by respiratory or gustatory sounds generated by the patient.

Figure 2:
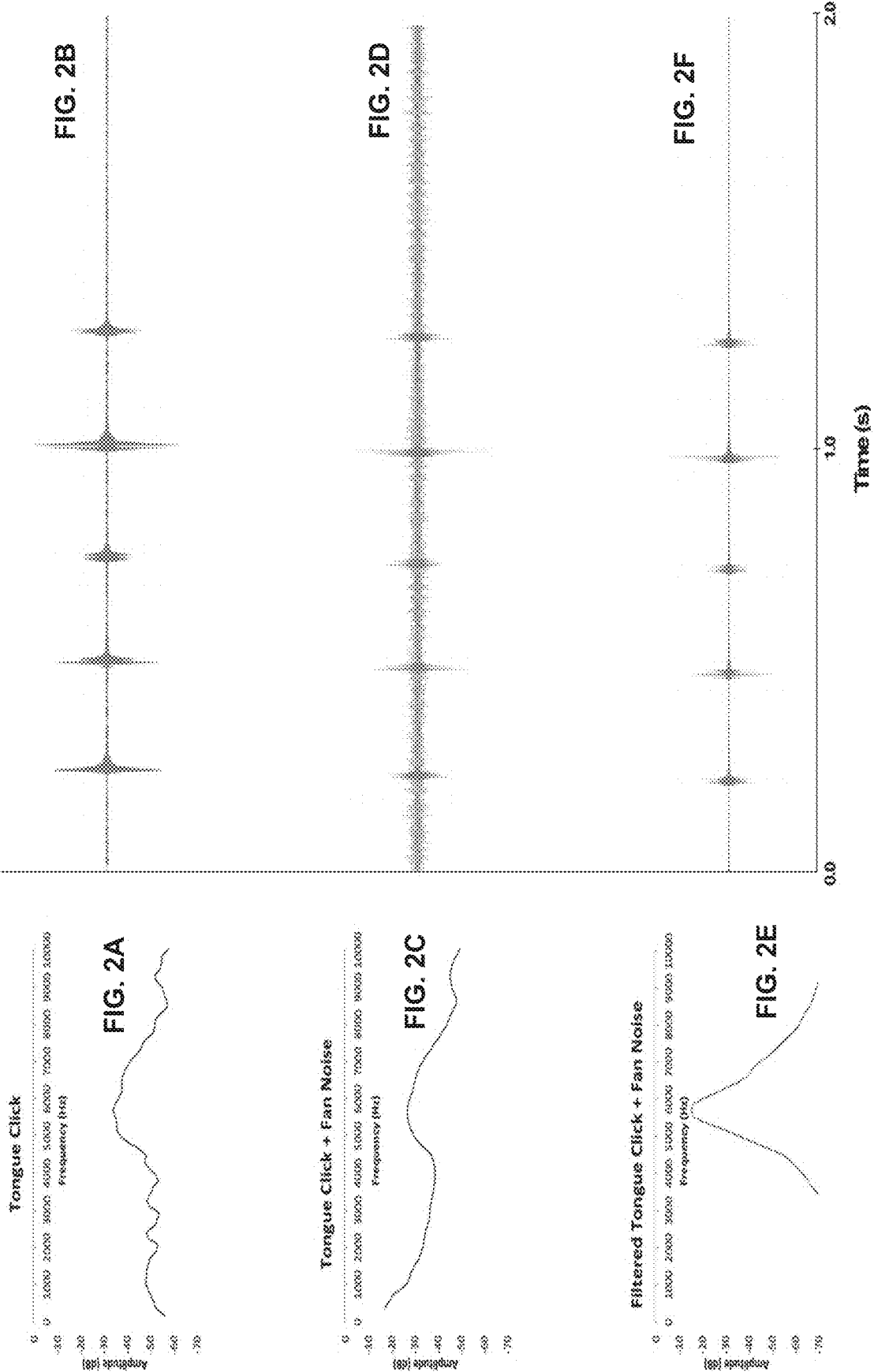
FIG. 2A illustrates average spectrum of a tongue click in frequency domain.
FIG. 2B illustrates signal intensity of tongue click in time domain.
FIG. 2C illustrates average spectrum of fan noise and tongue clicks in frequency domain.
FIG. 2D illustrates signal intensity of fan noise and tongue clicks in time domain.
FIG. 2E illustrates average spectrum of a filtered tongue click and fan noise in frequency domain.
FIG. 2F illustrates signal intensity of a filtered tongue click and fan noise in time domain.

The disclosed methods and systems can determine a characteristic of the intentional movements and generate a filter to account for the unintentional movements. For example, the methods and systems can employ an acoustic analysis of intentional sounds (e.g., the "small mouth" sounds) to determine a time domain and frequency domain signature. The disclosed methods and systems can apply a filter (e.g., digital filter, analog filter) to an audio signal picked up by an audio sensor in order to identify intentional inputs. By way of example, FIGS. 2A-2F illustrate signal and spectral characteristics of environmental noise and a target mouth sound. Specifically, FIG. 2A illustrates average spectrum of a tongue click in frequency domain. FIG. 2B illustrates signal intensity of tongue click in time domain. FIG. 2C illustrates average spectrum of fan noise and tongue clicks in frequency domain. FIG. 2D illustrates signal intensity of fan noise and tongue clicks in time domain. FIG. 2E illustrates average spectrum of a filtered tongue click and fan noise in frequency domain. FIG. 2F illustrates signal intensity of a filtered tongue click and fan noise in time domain. As shown in FIG. 2C and FIG. 2D, an intended tongue click is obscured by a background noise that is not desired, for example, fan noise. The signals representing a tongue click and a fan noise added together can be an input to a band-pass filter that would pass the characteristic frequencies of an intended tongue click. The output signal of the band-pass filter is shown in FIG. 2E and FIG. 2F. By defining a filter that can pass a desired predetermined frequency range, unintended false positive signal detections can be prevented.

Figure 3:
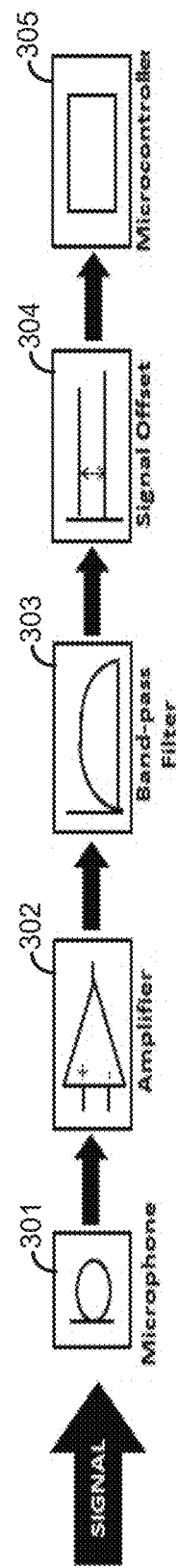
FIG. 3 is block diagram illustrating an audio signal detection method.

FIG. 3 is a block diagram of an exemplary audio signal detection algorithm. At block 301, an input signal can be received by an audio sensor, such as a microphone. At block 302, the input signal can be amplified and passed through a band-pass filter at block 303. At block 304, the filtered input signal can be offset and provided to a microcontroller at block 305. The audio input signal passes from the microphone to an amplifier and the band-pass filter whose cutoff frequencies are set to limit the signal to the frequency range of a targeted signal. The offset block 304 can be used since many signal processing chips operate only with positive voltages. The micro-controller can determine whether the input signal meets a characteristic (e.g., temporal characteristic) of an intended target signal and/or whether the input signal included one or more of the targeted signals.

Figure 4A:
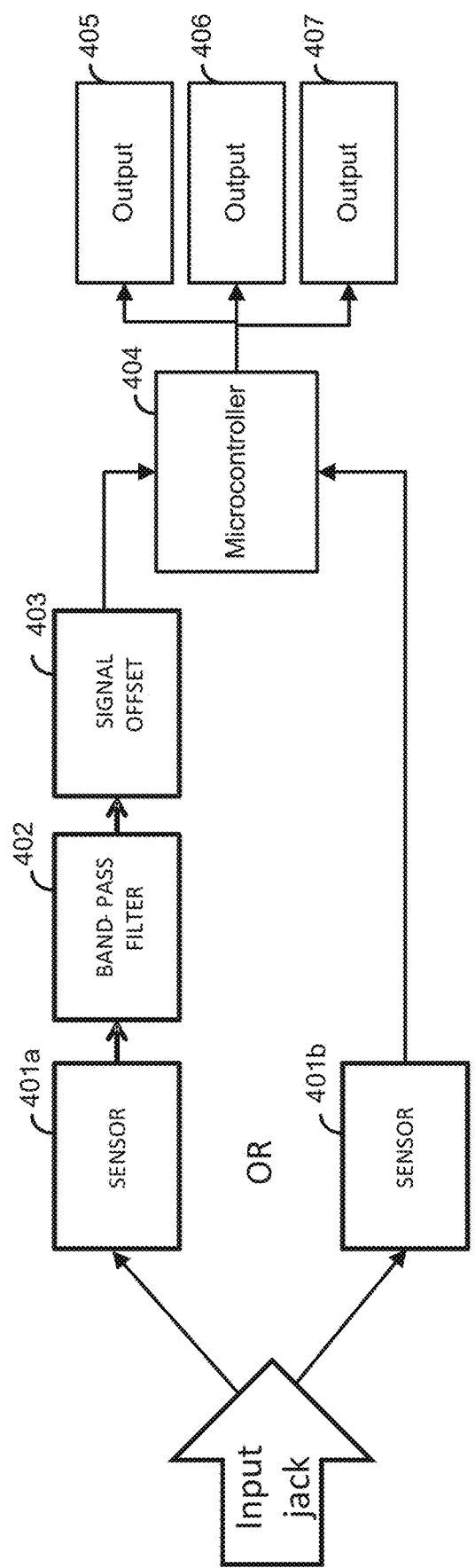
FIG. 4A illustrates an example apparatus using analog filtering.

In an aspect, illustrated in FIG. 4A, provided an example apparatus using analog filtering. One or more sensors (e.g., sensor 401a) can be configured to receive one or more input signals via an input jack. For example, the modality of the one or more signals can comprise audio, tactile, pressure, IR reflectance, and the like. The one or more input signals can be applied to a filter (e.g., band-pass filter) 402. For example, rather than responding each time a user touches a switch plate, the band-pass filter 402 can effectively filter out the unintentional touches and only respond to an intentional touch. In an aspect, the filter 402 can be generated by identifying an intentional gesture based on characteristics of the intentional gesture in the frequency domain, the time domain, or both. An offset can be applied to the filter input signal at block 403. The processed input signal can be transmitted to a microcontroller 404. In another aspect, an input signal does not need to be processed by the band-pass filter 402 and/or offset sensor 403. For example, input signal can be received by sensor 401b and transmitted to the microcontroller 404 directly (e.g., via an unfiltered channel). In an aspect, the microcontroller 404 can comprise one or more gesture detectors. In an aspect, the microcontroller 404 can not only detect the presence of an intentional input but can also track a number of inputs (intentional and/or unintentional) produced in succession. For example, one input signal (such as a first tap, a first blink, a first pressure bulb squeeze, or a first small mouth sound) can be used to activate a nurse call, while two input signals (e.g., such as a second tap, a second blink, a second pressure bulb squeeze, or a second small mouth sound) can be used to control an additional device (such as a fan or light), and three input signals (e.g., such as a third tap, a third blink, a third pressure bulb squeeze, or a third small mouth sound) can control yet another one or more devices (such as a TV). This allows a user who can only produce a single gesture to directly control a number of devices. As an example, a first intentional input can be sent to the output interface 405 for control a first device (e.g., nurse call). A second intentional input can be sent to the output interface 406 for control a second device (e.g., TV). A third intentional input can be sent to the output interface 407 for control a third device (e.g., computer). In an aspect, any number of output interfaces can be configured to control any number of devices.

Figure 4B:
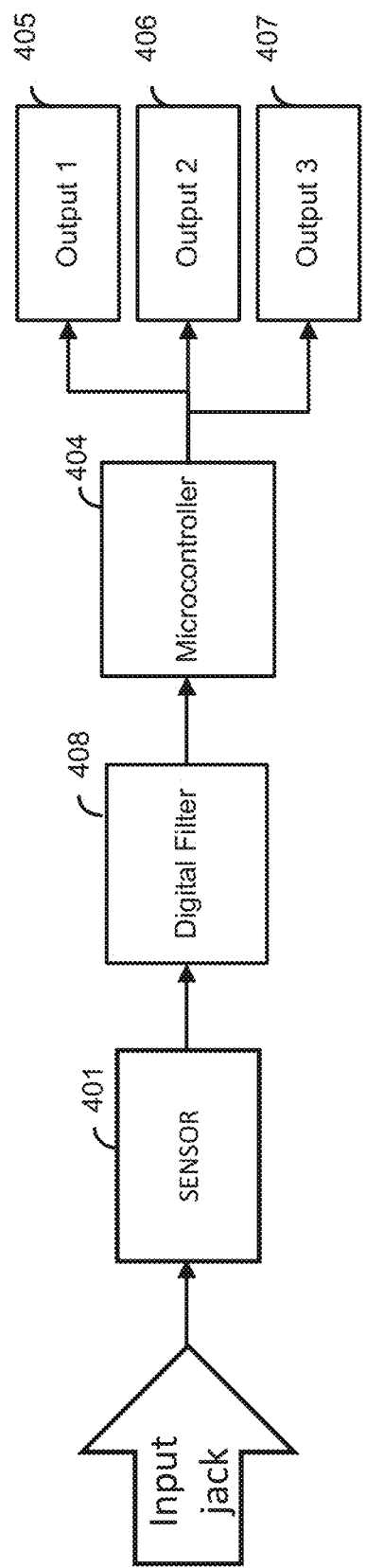
FIG. 4B illustrates an example apparatus using digital filtering.

In an aspect, illustrated in FIG. 4B, provided an example apparatus using digital filtering. As an example, a digital filter 408 can be applied to the input signals received via sensor 401. The digitally filtered input signals can be transmitted to the microcontroller 404. In an aspect, the microcontroller 404 can comprise one or more gesture detectors. In an aspect, the microcontroller 404 can not only detect the presence of an intentional input but can also track a number of inputs (intentional and/or unintentional) produced in succession. In an aspect, a first intentional input can be sent to the output interface 405 for control a first device (e.g., nurse call). A second intentional input can be sent to the output interface 406 for control a second device (e.g., TV). A third intentional input can be sent to the output interface 407 for control a third device (e.g., computer).

Figure 5:
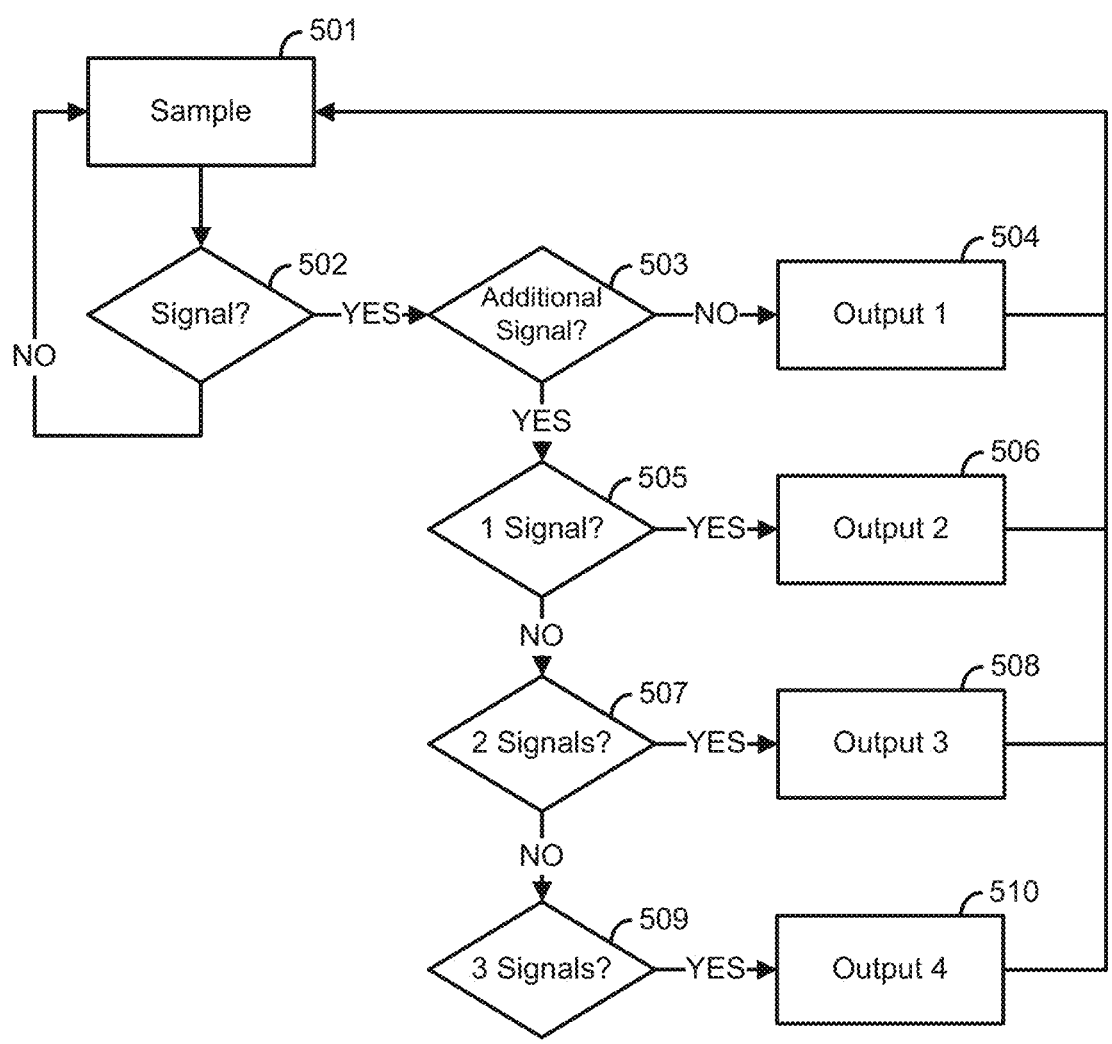
FIG. 5 illustrates the logic of a signal detection algorithm.

FIG. 5 illustrates the logic of a signal detection algorithm. At block 501, an input interface can be sampled to determine if a signal exists. If it is determined at block 502 that no signal exists, then methods can return to block 501. If a signal exists, the methods can proceed to block 503 to determine if a subsequent signal exists. If no subsequent signal exists, the methods can generate an output at block 504 and return to block 501. If an additional signal exists, it can be determined whether only one additional signal exists at block 505. If only one additional signal exists, the methods can generate an output at block 506 and return to block 501. If an additional signal exists, it can be determined whether only two additional signals exist at block 507. If only two additional signals exist, the methods can generate an output at block 506 and return to block 501. If an additional signal exists, it can be determined whether only three additional signals exist at block 509. If only three additional signals exist, the methods can generate an output at block 510 and return to block 501. A variety of inputs can be utilized and a variety of outputs can be generated at each signal processing step.

The present methods and systems can be operational with numerous other general purpose or special purpose computing system environments or configurations. Examples of well known computing systems, environments, and/or configurations that can be suitable for use with the systems and methods comprise, but are not limited to, personal computers, server computers, laptop devices, and multiprocessor systems. Additional examples comprise set top boxes, programmable consumer electronics, network PCs, minicomputers, mainframe computers, distributed computing environments that comprise any of the above systems or devices, and the like.

Figure 6:
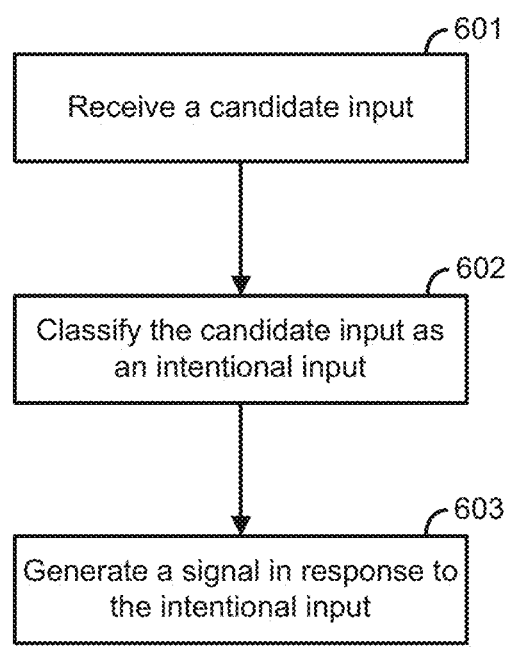
FIG. 6 is a flow chart illustrating an exemplary method.

In an aspect, illustrated in FIG. 6, provided are methods for communication. At block 601, a candidate input can be received. In an aspect, a candidate input can be received from one or more sensors. As an example, the one or more sensors can comprise one or more of a touch sensor, a pressure sensor (e.g., oral pressure sensor), an optical reflectance sensor (e.g., infrared reflectance sensor), an electromyography (EMG) sensor, a light sensor, a proximity detector, an audio sensor, a mechanical sensor, a capacitance sensor, a camera, and the like. In an aspect, any type of sensor and any type of output can be utilized. In an aspect, a candidate input can be received from binary switches such as push buttons, capacitive touches, squeeze switches, and the like.

At block 602, the candidate input can be classified as an intentional input. In an aspect, classifying the candidate input as an intentional input can comprise determining a characteristic of an intentional input, generating a filter based on the characteristic, and applying the filter to the candidate input. In an aspect, the characteristic can be derived from a frequency domain, a time domain, or both.

Such time-domain and frequency-domain characteristics can comprise properties such as a time domain intensity envelope and/or a frequency domain spectral shape. As an example, the candidate input can be processed by a signal processor 102 to classify a specific stimulus as intentional, as distinguished from noise and unintentional stimuli.

As an example, a characteristic of a tremor can be determined and processed to generate a filter. For example, a tremor can generate a signal from about 4 Hz to about 12 Hz, for example a 4 Hz, 5 Hz, 6 Hz, 7 Hz, 8 Hz, 9 Hz, 10 Hz, 11 Hz, and/or 12 Hz signal. An intentional tremor can have a frequency of below about 5 Hz. A low pass filter can be applied to the signal received from a touch switch to account for the tremors.

As an example, a characteristic of a pressure can be determined and processed to generate a filter. For example, the time course of an intentional lip closing gesture and magnitude of the pressure changes associated with the intentional lip closing gesture can be analyzed. For example, the intentional biting down on the bulb will generate a significantly larger pressure change than the inadvertent rolling of the tongue over the bulb. A filter can be generated to discriminate between intentional and unintentional inputs based on particular pressure changes over a particular time interval. For example, a temporal filter can distinguish the rapid changes in pressure associated with an intentional oral gesture from the slower changes in pressure associated with a non-intentional oral gesture. The temporal filter can also distinguish larger magnitude pressure changes from the smaller pressure changes that may be associated with accidental compression of a sylastic bulb used to detect oral movements.

As another example, a characteristic of an eyelid movement can be determined and processed to generate a filter. For example, eye-blink switches can be utilized that detects changes in reflected infrared light that are a consequence of eyelid movements. In an aspect, kinematic analysis of eyelid movements for blink detection can be used to set temporal cutoffs that only respond to the reflectance changes associated with the intermediate temporal duration of the intentional blink/wink.

As another example, a characteristic of a sound can be determined and processed to generate a filter. A filter can be generated to discriminate between the sounds made by small tongue movements and ambient noise. Two modes of filtering can be used, specifically, a filter in the frequency domain and a filter in the time domain. For example, a candidate signal can be first passed through a band-pass filter to eliminate candidate signals that are not in a known frequency range of the intentional gesture sound. However, other environmental noises may occur in similar frequency ranges as the intentional gesture sounds, accordingly, a temporal filtering can also be applied. For example, background noises can be of random temporal durations, while the intentional gesture sounds can be of known temporal durations. Therefore, by ignoring candidate signals that fall within a desired frequency range of the intentional gesture sounds and distinguishing temporal durations longer or shorter than a predetermined duration associated with an intentional gesture sound, the amount of false positive intentional inputs can be further reduced.

At block 603, a signal can be generated in response to the intentional input. In an aspect, generating a signal in response to the intentional input can comprise activating a nurse call switch. In another aspect, generating a signal in response to the intentional input can comprise controlling one or more controlled devices. A controlled device can comprise one or more of a nurse call switch, a computer, a television, a telephone, a medical device, an application (e.g., iPad applications), a speech generating device, and the like. In an aspect, the generated signal can be used as keyboard commands for communication or controlling other mechanical or computerized outputs. In an aspect, the signal can comprise an optional visual output. The visual output can be displayed as a menu of instructions and options.

Figure 7:
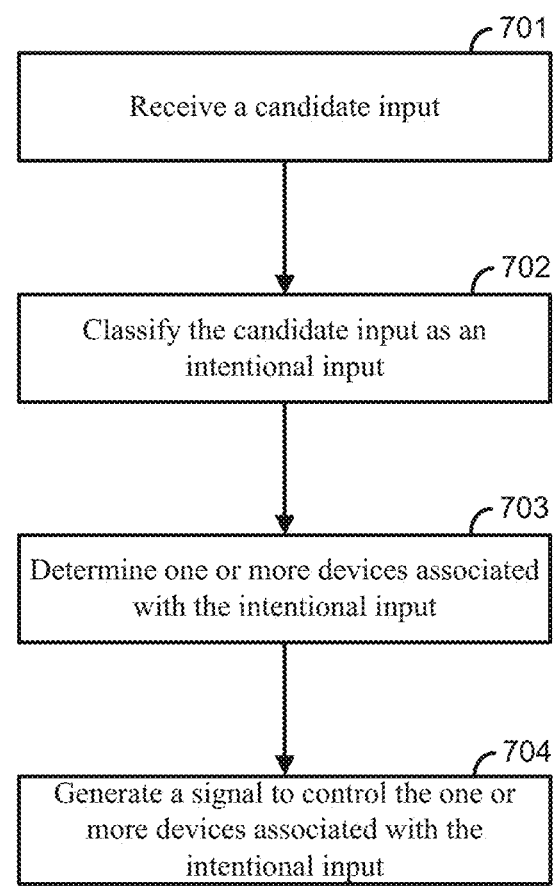
FIG. 7 is a flow chart illustrating an exemplary method.

In an aspect, illustrated in FIG. 7, provided are methods for communication. At block 701, a candidate input can be received. In an aspect, a candidate input can be received from one or more sensors. As an example, the one or more sensors can comprise one or more of a touch sensor, a pressure sensor (e.g., oral pressure sensor), an optical reflectance sensor (e.g., infrared reflectance sensor), an electromyography (EMG) sensor, a light sensor, a proximity detector, an audio sensor, a mechanical sensor, a capacitance sensor, a camera, and the like. In an aspect, any type of sensor and any type of output can be utilized.

At block 702, the candidate input can be classified as an intentional input. In an aspect, classifying the candidate input as an intentional input can comprise determining a characteristic of an intentional input, generating a filter based on the characteristic, and applying the filter to the candidate input. In an aspect, the characteristic can be derived from a frequency domain, a time domain, or both. Such time-domain and frequency-domain characteristics can comprise properties such as a time domain intensity envelope and/or a frequency domain spectral shape.

In an aspect, an intentional input can comprise one or more signals. For example, the intentional input can comprise one or more gestures (e.g., eye blinks) with certain characteristics. As another example, the intentional input can comprise a sequence of gestures (e.g., eye blink followed by a tap). The intentional input can be used to control one or more devices. As an example, the candidate input can be processed by a signal processor 102 to classify a specific stimulus as intentional, as distinguished from noise and unintentional stimuli.

As an example, a characteristic of a tremor can be determined and processed to generate a filter. For example, a tremor can generate a signal from about 4 Hz to about 12 Hz, for example a 4 Hz, 5 Hz, 6 Hz, 7 Hz, 8 Hz, 9 Hz, 10 Hz, 11 Hz, and/or 12 Hz signal. An intentional tremor can have a frequency of below about 5 Hz. A low pass filter can be applied to the signal received from a touch switch to account for the tremors.

As an example, a characteristic of a pressure can be determined and processed to generate a filter. For example, the time course of an intentional lip closing gesture and magnitude of the pressure changes associated with the intentional lip closing gesture can be analyzed. For example, the intentional biting down on the bulb will generate a significantly larger pressure change than the inadvertent rolling of the tongue over the bulb. A filter can be generated to discriminate between intentional and unintentional inputs based on particular pressure changes over a particular time interval. For example, a temporal filter can distinguish the rapid changes in pressure associated with an intentional oral gesture from the slower changes in pressure associated with a non-intentional oral gesture. The temporal filter can also distinguish larger magnitude pressure changes from the smaller pressure changes that may be associated with accidental compression of a sylastic bulb used to detect oral movements.

As another example, a characteristic of an eyelid movement can be determined and processed to generate a filter.

For example, eye-blink switches can be utilized that detects changes in reflected infrared light that are a consequence of eyelid movements. In an aspect, kinematic analysis of eyelid movements for blink detection can be used to set temporal cutoffs that only respond to the reflectance changes associated with the intermediate temporal duration of the intentional blink/wink.

As another example, a characteristic of a sound can be determined and processed to generate a filter. A filter can be generated to discriminate between the sounds made by small tongue movements and ambient noise. Two modes of filtering can be used, specifically, a filter in the frequency domain and a filter in the time domain. For example, a candidate signal can be first passed through a band-pass filter to eliminate candidate signals that are not in a known frequency range of the intentional gesture sound. However, other environmental noises may occur in similar frequency ranges as the intentional gesture sounds, accordingly, a temporal filtering can also be applied. For example, background noises can be of random temporal durations, while the intentional gesture sounds can be of known temporal durations. Therefore, by ignoring candidate signals that fall within a desired frequency range of the intentional gesture sounds and distinguishing temporal durations longer or shorter than a predetermined duration associated with an intentional gesture sound, the amount of false positive intentional inputs can be further reduced.

At block 703, one or more devices associated with the intentional input can be determined. For example, a microcontroller 404 can not only detect the presence of an intentional input but can also track a number of inputs (intentional and/or unintentional) produced in succession. For example, one input (a first intentional tap, a first intentional blink, a first intentional pressure bulb squeeze, or a first intentional small mouth sound) can be used to activate a nurse call, while two inputs (e.g., a second intentional tap, a second intentional blink, a second intentional pressure bulb squeeze, or a second intentional small mouth sound) can be used to control an additional device (e.g., a fan or light), and three inputs (e.g., a third intentional tap, a third intentional blink, a third intentional pressure bulb squeeze, or a third intentional small mouth sound) can control yet another additional device (e.g., a TV). In an aspect, this allows a user who can only produce a single gesture to directly control a number of devices.

In another aspect, a user can control one or more devices by a plurality of gestures. As an example, a sequence of gestures can be used to control a particular device. For example, an intentional tap followed by an intentional small mouth sound can control a television, while two intentional taps followed by an intentional small mouth sound can control a light. An intentional eye blink and an intentional small mouth sound can control a fan.

At block 704, one or more signals can be generated to control the one or more devices associated with the intentional input. As an example, controlling the one or more devices can comprise activating a nurse call switch. In another aspect, generating a signal in response to the intentional input can comprise controlling one or more controlled devices. A controlled device can comprise one or more of a nurse call switch, a computer, a television, a telephone, a medical device, an application (e.g., an iPad application), a speech generating device, and the like. In an aspect, the generated signal can be used as keyboard commands for communication or controlling other mechanical or computerized outputs. In an aspect, the one or more signals can comprise an optional visual output. The visual output can be displayed as a menu of instructions and options. As an example, the first signal can be generated to control a television, a second signal can be generated to control a light, and a third signal can be generated to control an air conditioning system.

Figure 8:
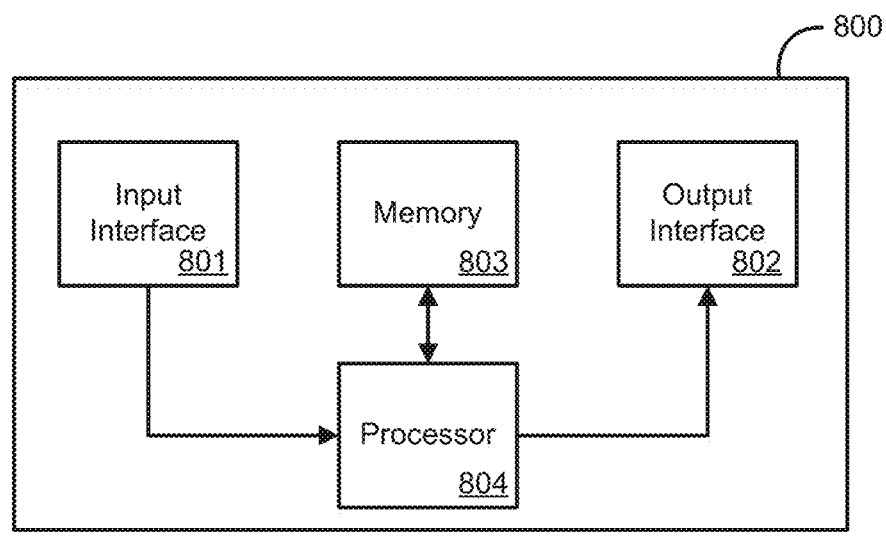
FIG. 8 is exemplary apparatus.

In an aspect, illustrated in FIG. 8, provided is an apparatus 800 for communication, comprising an input interface 801, configured for receiving candidate input from one or more sensors, an output interface 802, configured for transmitting a signal to a controlled device, a memory 803, configured for storing a filter, and a processor 804, coupled to the input interface 801, the output interface 802, and the memory 803. In an aspect, the processor 804 can be configured to perform steps comprising, classifying the candidate input received by the input interface by applying the filter stored in the memory, and providing the signal to the output interface for transmission to the controlled device.

In an aspect, the input interface 801 can comprise one or more of a serial port, a Universal Serial Bus port, a Bluetooth transceiver, an 802.xx transceiver, and the like. The output interface 802 can comprise one or more of a serial port, a Universal Serial Bus port, a Bluetooth transceiver, an 802.xx transceiver, and the like. In a further aspect, the processor 804 can be further configured to perform steps comprising determining a characteristic of an intentional input and generating a filter based on the characteristic. The characteristic can derived from one or more of a frequency domain and a time domain.

In an aspect, the memory 803 can stored filters and associated characteristics. When a candidate input is received, a filter can be retrieved from the memory 803 according to a characteristic of an intentional input. In an aspect, the characteristic can be derived from a frequency domain, a time domain, or combination thereof.

Figure 9:
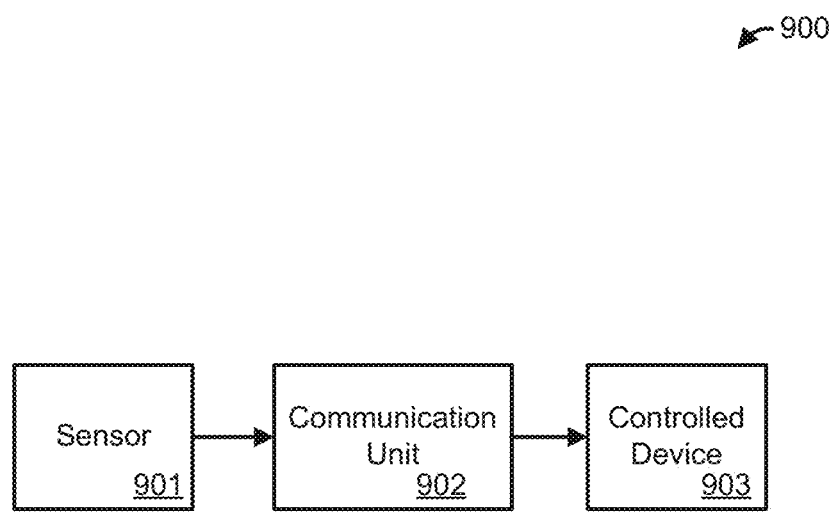
FIG. 9 is exemplary system.

In an aspect, illustrated in FIG. 9, provided are systems 900 for communication. The system 900 can comprise a sensor 901, configured for receiving one or more candidate inputs, and a communication unit 902 coupled to the sensor 901. In an aspect, the communication unit 902 can be configured to perform steps comprising, receive the one or more candidate inputs from the sensor 901, classify the one or more candidate inputs as one or more intentional inputs, and generating a signal in response to the one or more intentional inputs. The system 900 can further comprise a controlled device 903 coupled to the communication unit 902. In an aspect, the controlled device 903 can be configured to receive the signal generated by the communication unit 902. The controlled device 903 can comprise one or more of a nurse call switch, a computer, a television, a telephone, a medical device, and the like. The sensor 901 can be one or more of a touch sensor, a pressure sensor, an infrared reflectance sensor, a light sensor, a mechanical sensor, a capacitance sensor, a proximity detector, an audio sensor, a camera, and the like.

In an aspect, the communication unit 902 can be further configured to perform steps comprising determining a characteristic of the one or more intentional inputs, generating a filter based on the characteristic, and applying the filter to the one or more candidate inputs. The characteristic can be derived from a frequency domain, a time domain, or combination thereof.

Figure 10:
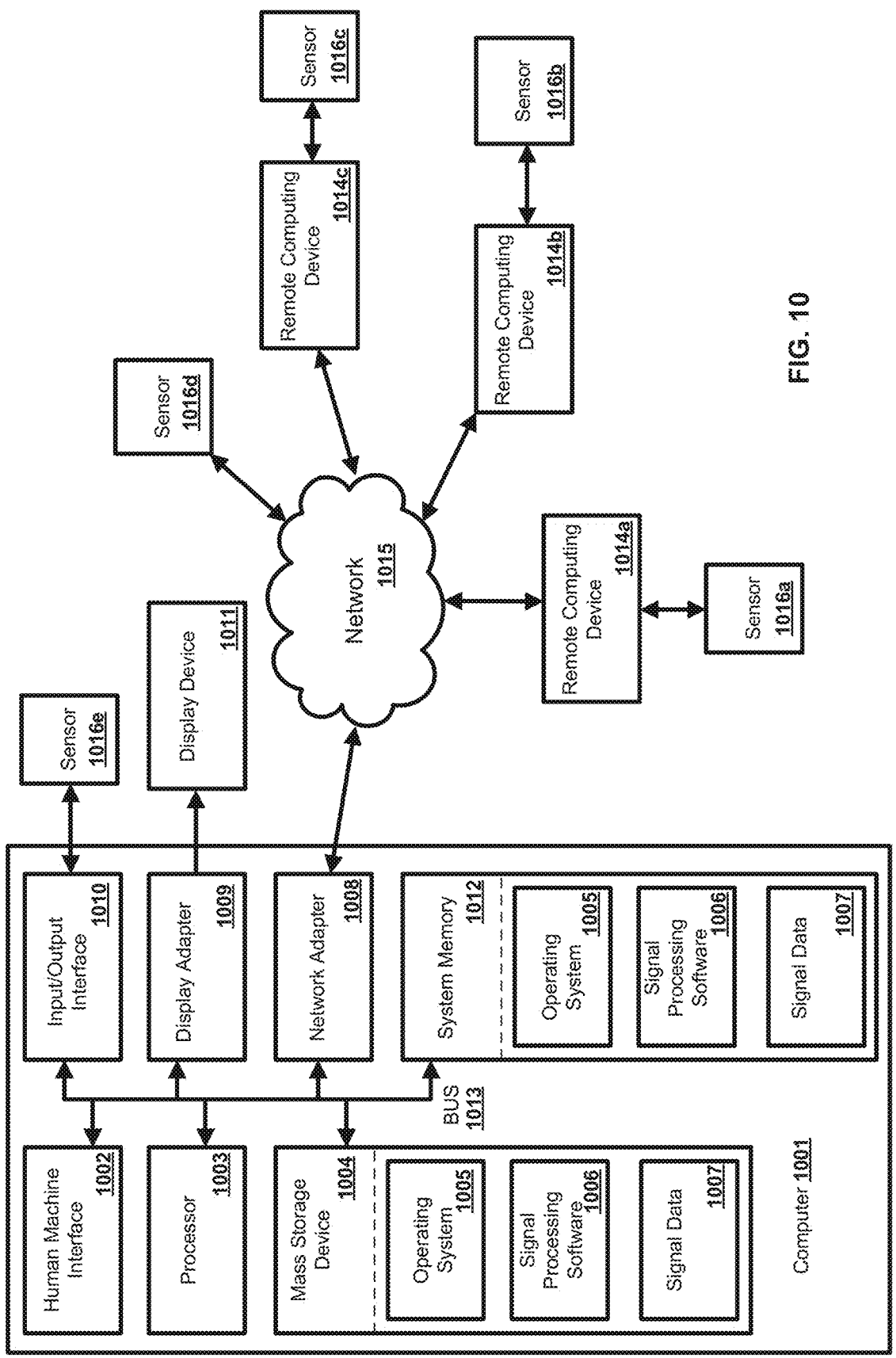
FIG. 10 is exemplary operating environment.

One skilled in the art will appreciate that provided is a functional description and that the respective functions can be performed by software, hardware, or a combination of software and hardware. The methods and systems can comprise the signal processing Software 1006 as illustrated in FIG. 10 and described below. In one exemplary aspect, the methods and systems can comprise a computer 1001 as illustrated in FIG. 10 and described below.

FIG. 10 is a block diagram illustrating an exemplary operating environment for performing the disclosed methods. This exemplary operating environment is only an example of an operating environment and is not intended to suggest any limitation as to the scope of use or functionality of operating environment architecture. Neither should the operating environment be interpreted as having any dependency or requirement relating to any one or combination of components illustrated in the exemplary operating environment.

The present methods and systems can be operational with numerous other general purpose or special purpose computing system environments or configurations. Examples of well known computing systems, environments, and/or configurations that can be suitable for use with the systems and methods comprise, but are not limited to, personal computers, server computers, laptop devices, and multiprocessor systems. Additional examples comprise set top boxes, programmable consumer electronics, network PCs, minicomputers, mainframe computers, distributed computing environments that comprise any of the above systems or devices, and the like.

The processing of the disclosed methods and systems can be performed by software components. The disclosed systems and methods can be described in the general context of computer-executable instructions, such as program modules, being executed by one or more computers or other devices. Generally, program modules comprise computer code, routines, programs, objects, components, data structures, etc. that perform particular tasks or implement particular abstract data types. The disclosed methods can also be practiced in grid-based and distributed computing environments where tasks are performed by remote processing devices that are linked through a communications network. In a distributed computing environment, program modules can be located in both local and remote computer storage media including memory storage devices.

Further, one skilled in the art will appreciate that the systems and methods disclosed herein can be implemented via a general-purpose computing device in the form of a computer 1001. The components of the computer 1001 can comprise, but are not limited to, one or more processors or processing units 1003, a system memory 1012, and a system bus 1013 that couples various system components including the processor 1003 to the system memory 1012. In the case of multiple processing units 1003, the system can utilize parallel computing.

The system bus 1013 represents one or more of several possible types of bus structures, including a memory bus or memory controller, a peripheral bus, an accelerated graphics port, and a processor or local bus using any of a variety of bus architectures. By way of example, such architectures can comprise an Industry Standard Architecture (ISA) bus, a Micro Channel Architecture (MCA) bus, an Enhanced ISA (EISA) bus, a Video Electronics Standards Association (VESA) local bus, an Accelerated Graphics Port (AGP) bus, and a Peripheral Component Interconnects (PCI), a PCI-Express bus, a Personal Computer Memory Card Industry Association (PCMCIA), Universal Serial Bus (USB) and the like. The bus 1013, and all buses specified in this description can also be implemented over a wired or wireless network connection and each of the subsystems, including the processor 1003, a mass storage device 1004, an operating system 1005, signal processing software 1006, signal data 1007, a network adapter 1008, system memory 1012, an Input/Output Interface 1010, a display adapter 1009, a display device 1011, and a human machine interface 1002, can be contained within one or more remote computing devices 1014$a,b,c$ at physically separate locations, connected through buses of this form, in effect implementing a fully distributed system.

The computer 1001 typically comprises a variety of computer readable media. Exemplary readable media can be any available media that is accessible by the computer 1001 and comprises, for example and not meant to be limiting, both volatile and non-volatile media, removable and non-removable media. The system memory 1012 comprises computer readable media in the form of volatile memory, such as random access memory (RAM), and/or non-volatile memory, such as read only memory (ROM). The system memory 1012 typically contains data such as signal data 1007 and/or program modules such as operating system 905 and signal processing software 1006 that are immediately accessible to and/or are presently operated on by the processing unit 1003.

In another aspect, the computer 1001 can also comprise other removable/non-removable, volatile/non-volatile computer storage media. By way of example, FIG. 10 illustrates a mass storage device 1004 which can provide non-volatile storage of computer code, computer readable instructions, data structures, program modules, and other data for the computer 1001. For example and not meant to be limiting, a mass storage device 1004 can be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Optionally, any number of program modules can be stored on the mass storage device 1004, including by way of example, an operating system 1005 and signal processing software 1006. Each of the operating system 1005 and signal processing software 1006 (or some combination thereof) can comprise elements of the programming and the signal processing software 1006. Signal data 1007 can also be stored on the mass storage device 1004. Signal data 1007 can be stored in any of one or more databases known in the art. Examples of such databases comprise, DB2®, Microsoft® Access, Microsoft® SQL Server, Oracle®, mySQL, PostgreSQL, and the like. The databases can be centralized or distributed across multiple systems.

In another aspect, the user can enter commands and information into the computer 1001 via an input device (not shown). Examples of such input devices comprise, but are not limited to, a keyboard, pointing device (e.g., a "mouse"), a microphone, a joystick, a scanner, tactile input devices such as gloves, and other body coverings, and the like These and other input devices can be connected to the processing unit 1003 via a human machine interface 1002 that is coupled to the system bus 1013, but can be connected by other interface and bus structures, such as a parallel port, game port, an IEEE 1394 Port (also known as a Firewire port), a serial port, or a universal serial bus (USB).

In yet another aspect, a display device 1011 can also be connected to the system bus 1013 via an interface, such as a display adapter 1009. It is contemplated that the computer 1001 can have more than one display adapter 1009 and the computer 1001 can have more than one display device 1011. For example, a display device can be a monitor, an LCD (Liquid Crystal Display), or a projector. In addition to the display device 1011, other output peripheral devices can comprise components such as speakers (not shown) and a printer (not shown) which can be connected to the computer 1001 via Input/Output Interface 1010. Any step and/or result of the methods can be output in any form to an output device. Such output can be any form of visual representation, including, but not limited to, textual, graphical, animation, audio, tactile, and the like. The display 1011 and computer 1001 can be part of one device, or separate devices.

One or more sensors 1016a-e can be configured to provide input to computer 1001 through the input/output interface 1010 and/or the network adapter 1008. The computer 1001 can receive inputs from sensors directly connected to the computer 1001 and through the network 1015.

The computer 1001 can operate in a networked environment using logical connections to one or more remote computing devices 1014a,b,c. By way of example, a remote computing device can be a personal computer, portable computer, smartphone, a server, a router, a network computer, a peer device or other common network node, and so on. Logical connections between the computer 1001 and a remote computing device 1014a,b,c can be made via a network 1015, such as a local area network (LAN) and/or a general wide area network (WAN). Such network connections can be through a network adapter 1008. A network adapter 1008 can be implemented in both wired and wireless environments. Such networking environments are conventional and commonplace in dwellings, offices, enterprise-wide computer networks, intranets, and the Internet.

For purposes of illustration, application programs and other executable program components such as the operating system 1005 are illustrated herein as discrete blocks, although it is recognized that such programs and components reside at various times in different storage components of the computing device 1001, and are executed by the data processor(s) of the computer. An implementation of signal processing software 1006 can be stored on or transmitted across some form of computer readable media. Any of the disclosed methods can be performed by computer readable instructions embodied on computer readable media. Computer readable media can be any available media that can be accessed by a computer. By way of example and not meant to be limiting, computer readable media can comprise "computer storage media" and "communications media." "Computer storage media" comprise volatile and non-volatile, removable and non-removable media implemented in any methods or technology for storage of information such as computer readable instructions, data structures, program modules, or other data. Exemplary computer storage media comprises, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer.

The methods and systems can employ Artificial Intelligence techniques such as machine learning and iterative learning. Examples of such techniques include, but are not limited to, expert systems, case based reasoning, Bayesian networks, behavior based AI, neural networks, fuzzy systems, evolutionary computation (e.g. genetic algorithms), swarm intelligence (e.g. ant algorithms), and hybrid intelligent systems (e.g. Expert inference rules generated through a neural network or production rules from statistical learning).

The following examples are put forth so as to provide those of ordinary skill in the art with a complete disclosure and description of how the devices and/or methods claimed herein are made and used, and are intended to be purely exemplary and are not intended to limit the scope of the methods and systems

EXAMPLES

In an aspect, the present methods and systems can be implemented via an example apparatus illustrated in FIG. 11-FIG. 21 and described in further detail herein. The apparatus can comprise the Noddle™ developed by Voxello. The apparatus can be configured to specifically address the needs of patients who can not generate the movement or force necessary to use existing switch technologies. The apparatus can be configured for a user with limited physical abilities. For example, the apparatus can allow the user to utilize whatever type of sensor that is compatible with the user's physical capabilities. The apparatus can allow users who can only generate a single physical gesture to control multiple devices. This functionality is useful, for instance, for a user who can only blink one eye to be able to independently and simultaneously control a nurse call, television, fan and a speech generating device. The example apparatus can perform this functionality based on counting the number of times the user produces a gesture within a specified time window.

In an aspect, the apparatus can be configured to detect the smallest intentional gestures (e.g., tongue clicks, finger taps, eye blinks, applying minimal force to a low pressure sensing bulb). The apparatus can be configured to allow a patient, with a single switch, to control multiple devices, such as existing nurse call systems, speech-generating devices (SGD), patient controlled analgesia pumps, bed controls, telecommunication devices, environmental control systems, entertainment systems, and/or the like.

In an aspect, the apparatus can be configured to accept a range of sensors (e.g., Noddle-mic™, Noddle-touch™, and many $3^{rd}$ party switches) that can transduce whatever intentional gesture a patient can produce. The apparatus can be configured to use a gesture detection algorithm (e.g., as described herein) that filters out background noise and patients' unintentional gestures. Depending on whether a single gesture or sequence of gestures is detected, the apparatus can control at least three output devices. For example, the apparatus can communicate with the output devices via physical network links (e.g., serial or network communication) and/or wireless network links (e.g., via Bluetooth, WiFi, DEQ, Z-wave, or possibly new wireless technology in the future). For example, one intentional tongue click could activate the nurse call system, while two and three successive tongue clicks can be used to control a SGD (e.g., using the two-switch scanning mode). Therefore, an intensive care patient who cannot move or speak can use the apparatus to contact a nurse and also use a speech-generating device to communicate about pain or respiratory distress. Finally, the advantage of the apparatus over other "single" switches on the market is that patients would be able to take advantage of a "two-switch" scanning mode that allows them to enhance their communication rate by reducing the number of gestures needed to get to the desired message. In two-switch scanning the patient can move through a set of communication options by activating one switch and can then select to output an option by activating a second switch. For example, an output command (e.g., or signal) can be selected, and then the output device (e.g., or output port) can be selected. As another example, an output device (e.g., or output port) can be selected, and then an output command can be selected to output to the selected output device. The available commands for selection can be determined (e.g., or vary) based on the selected output device. The available output devices for selection can be determined (e.g., or vary) based on the selected output command.

Figure 11A:
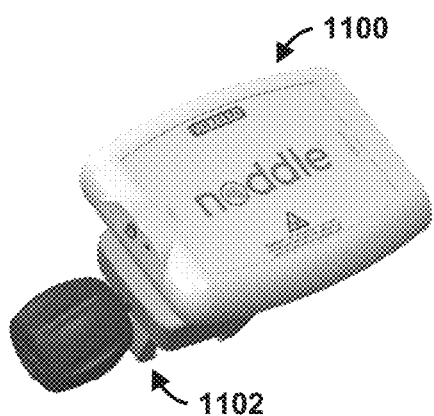
FIG. 11A shows a top-down perspective view of an example apparatus and a clamp.
Figure 11B:
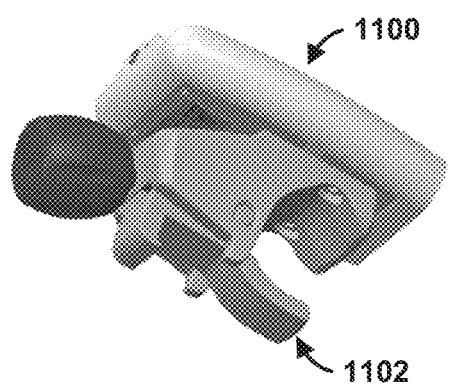
FIG. 11B shows a bottom-up perspective view of the example apparatus and the clamp.
Figure 11C:
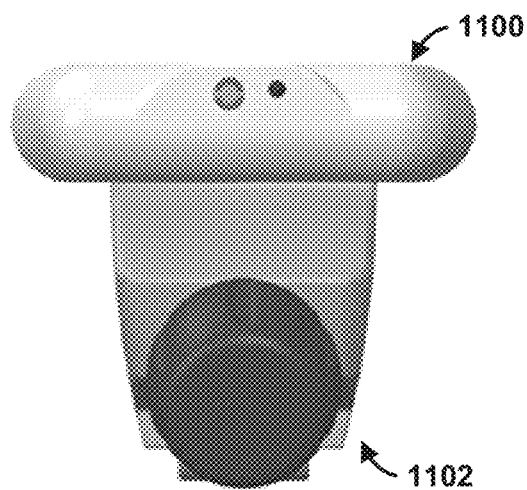
FIG. 11C shows a side-view of the example apparatus and the clamp.
Figure 11D:
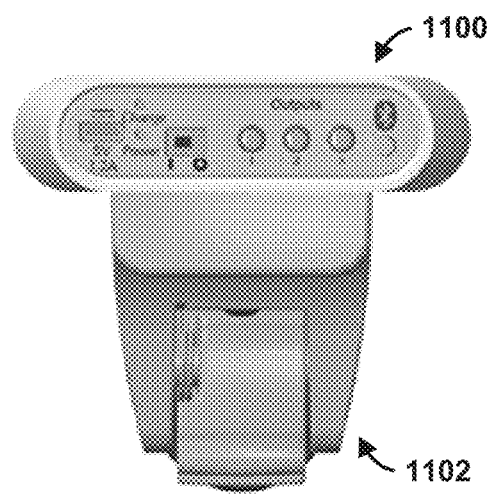
FIG. 11D shows another side-view of the example apparatus and the clamp.

FIG. 11A-FIG. 11B show multiple views of an example apparatus. FIG. 11A shows a top-down perspective view of the apparatus 1100 and a clamp 1102. The clamp 1102 can comprise a pole clamp configured to mount the apparatus to a structure, such as a pole used for administering IV fluids. FIG. 11B shows a bottom-up perspective view of the apparatus 1100 and the clamp 1102. FIG. 11C shows a side-view of the apparatus 1100 and the clamp 1102. FIG. 11D shows another side-view of the apparatus 1100 and the clamp 1102.

Figure 12A:
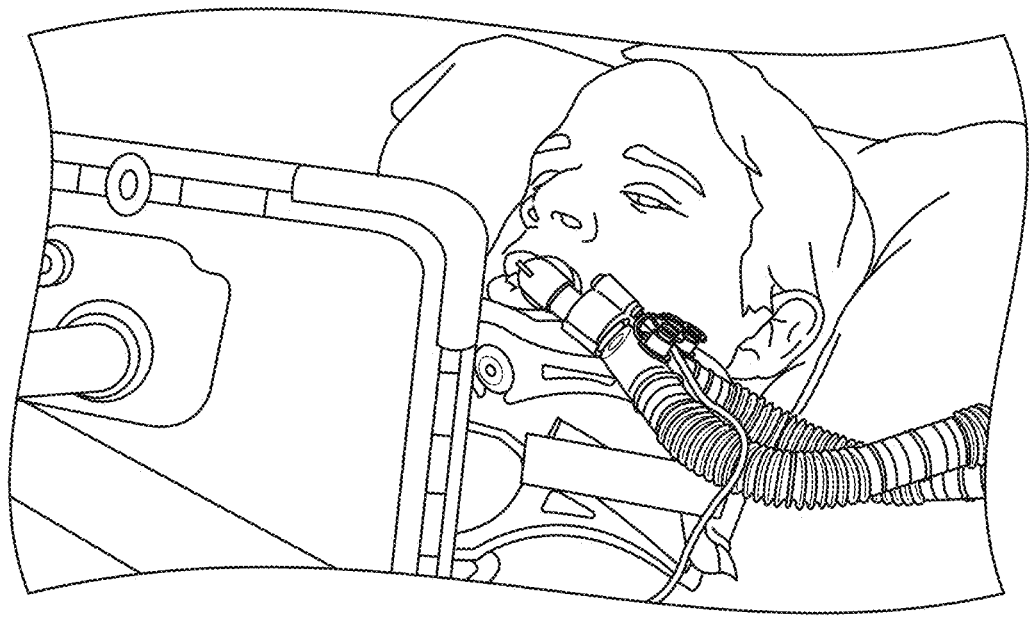
FIG. 12A shows an example sensor mounting.
Figure 12B:
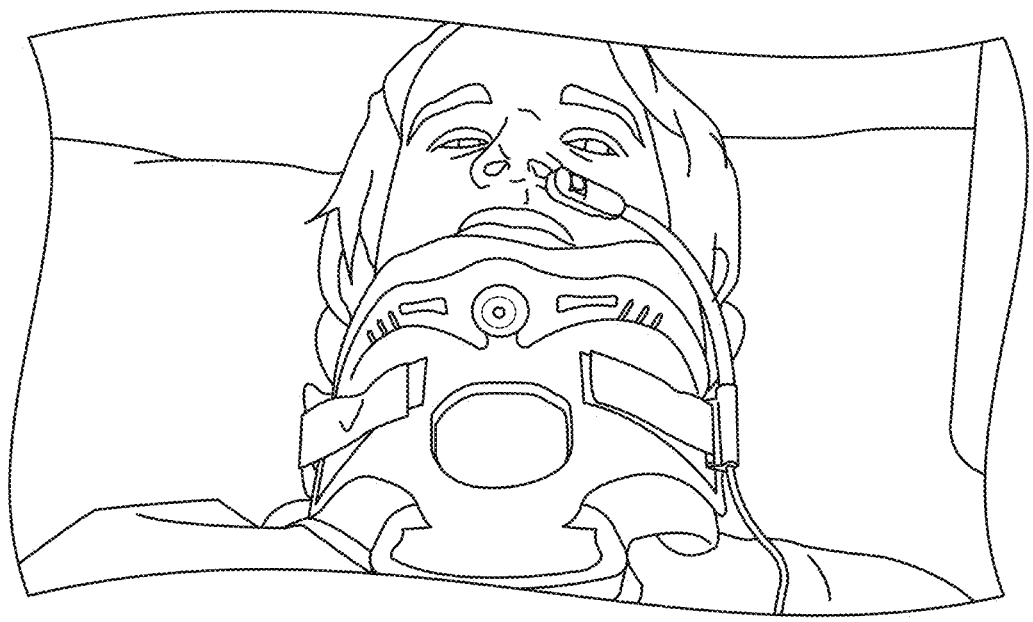
FIG. 12B shows an another example sensor mounting.
Figure 12C:
FIG. 12C shows an another example sensor mounting.
Figure 12D:
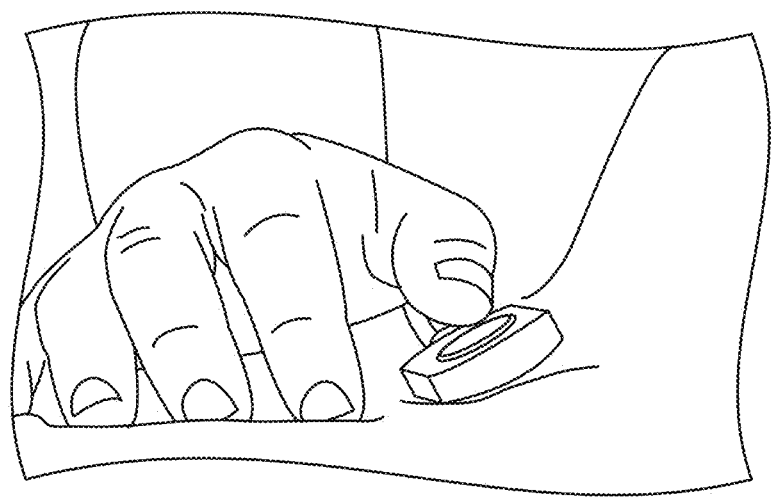
FIG. 12D shows an another example sensor mounting.

FIG. 12A-FIG. 12D illustrate some mounting options of sensors (e.g., Noddle-mic™ and Noddle-touch™ sensors) coupled with the apparatus. Example sensors can be mounted on a brace (e.g., a Miami-J collar), a vent line, bedding and/or the like. FIG. 12A shows a sensor mounted on a vent line. FIG. 12B shows a sensor mounted on a brace. FIG. 12C shows a sensor mounted on a brace. FIG. 12D shows a sensor mounted on bedding.

Figure 13A:
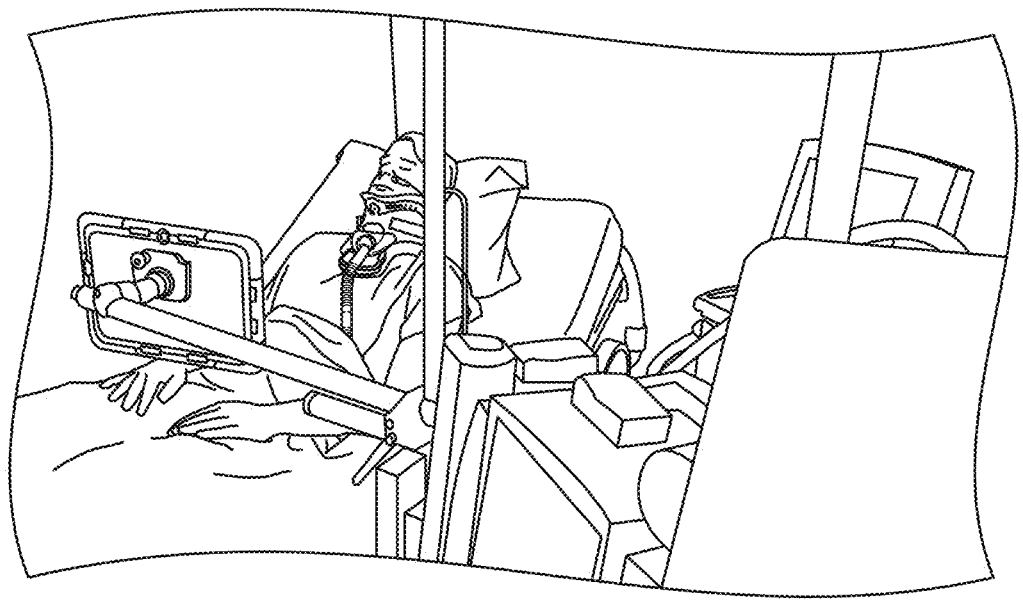
FIG. 13A illustrates an example apparatus with an pole mounted speech generating device.
Figure 13B:
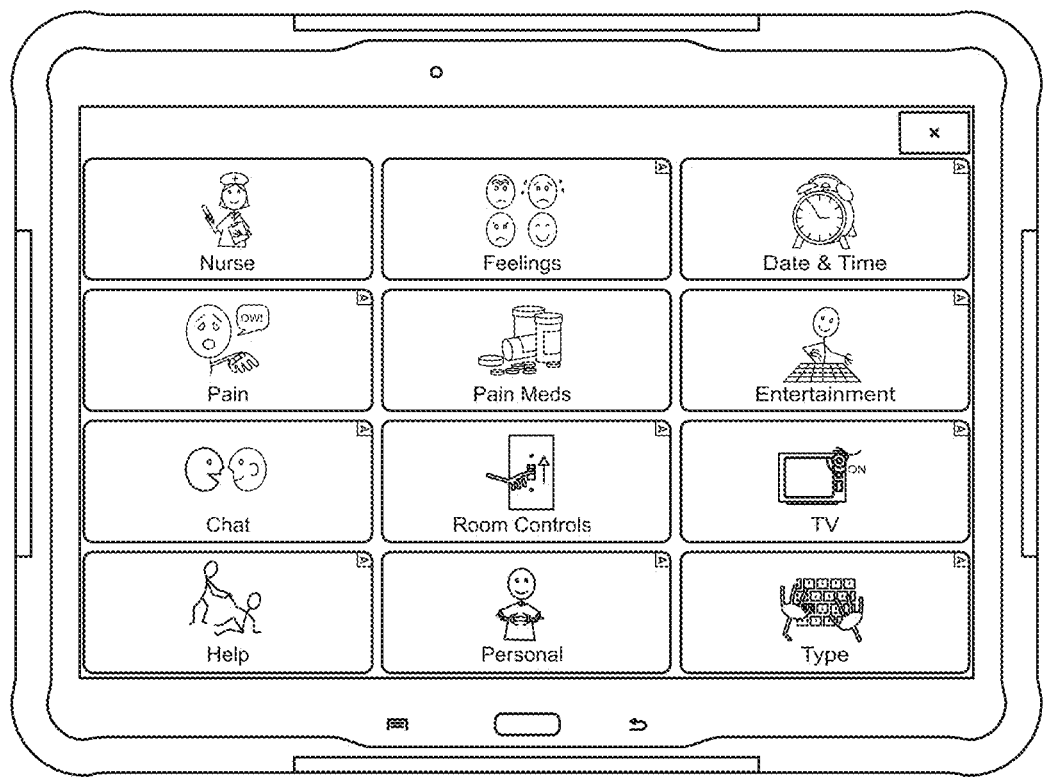
FIG. 13B illustrates an example user interface provided by the display.
Figure 13C:
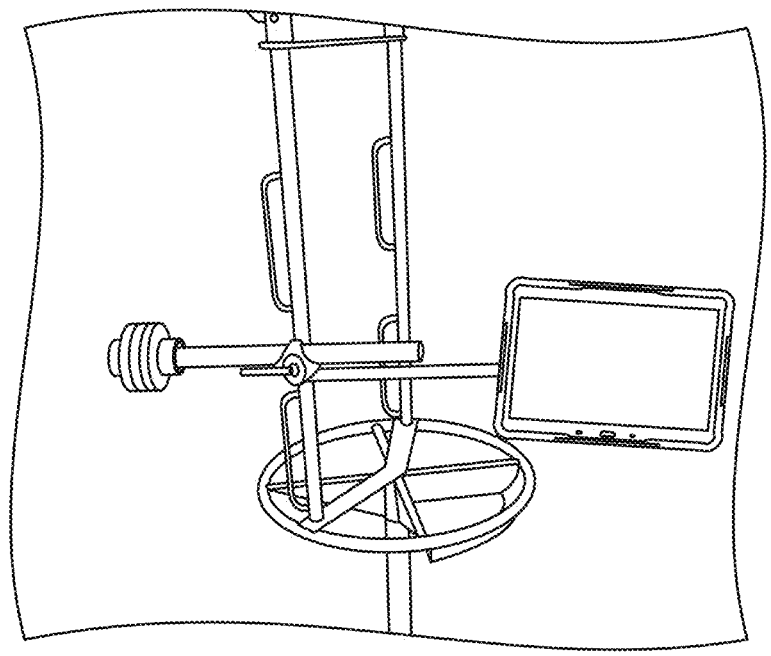
FIG. 13C shows another view of the mounting device and display device.

FIG. 13A illustrates an example apparatus with an IV pole mounted speech generating device (e.g., Noddle-chat™) and customized mounting device (e.g., Noddle-arm™) mounted on an IV pole. The mounting device allows a display to be provided to a user for easier control of multiple output devices. FIG. 13B illustrates an example user interface provided by the display. FIG. 13C shows another view of the mounting device and display device. The mounting device is attached to an IV pole via a clamp.

In an aspect, the apparatus can be used without calibration and can effectively be a "plug-and-play" device. The apparatus can be configured to automatically sense the type of sensor being used and apply the appropriate gesture detection algorithm. Since the apparatus is compatible with existing nurse call systems and speech-generating devices, the apparatus can be used in hospital and/or nursing home environments. The apparatus can be used with eye-tracking enabled SGDs. For example, patients with Amyotrophic Lateral Sclerosis (ALS), and other "locked in syndromes" can use the apparatus for communication. The primary obstacles to using eye trackers in acute care facilities involve calibrating the eye trackers, positioning the device at the bedside, and the added strain of having to maintain fixation to make a selection. Using the example apparatus would eliminate the added strain for patients who are able to use shift their gaze and use eye trackers.

Figure 14:
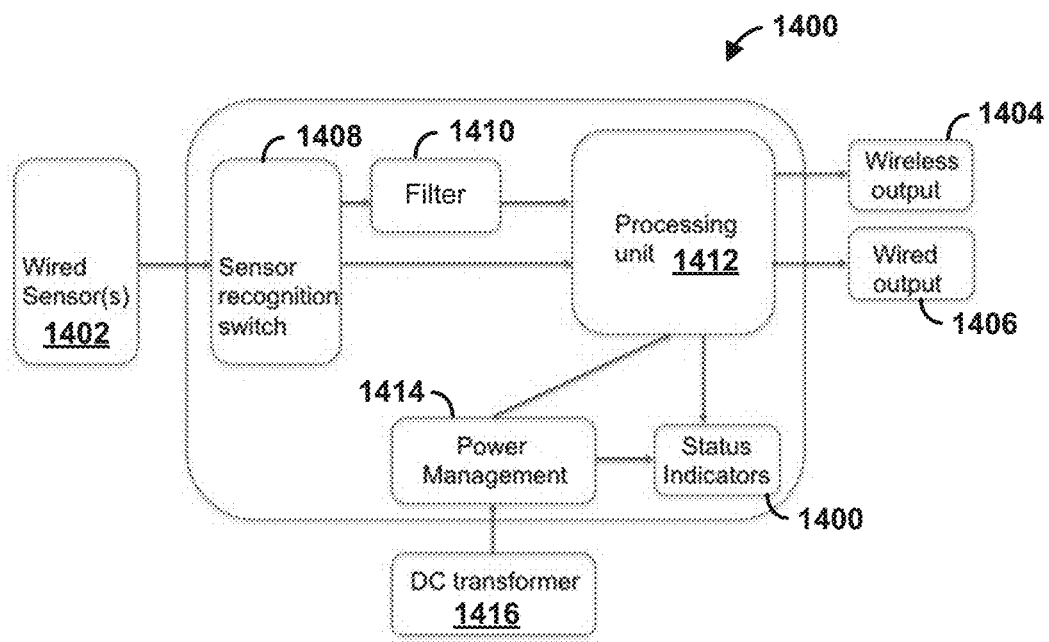
FIG. 14 is a block diagram illustrating an example apparatus.

The following provides, in more detail, example technical specifications for the apparatus. FIG. 14 is a block diagram illustrating an example apparatus 1400. The apparatus 1400 can be configured to receive input from wired sensors 1402. The apparatus 1400 can process that input and provide wired and/or wireless signals via a wireless output 1404 and/or a wired output 1406.

In an aspect, the apparatus 1400 can comprise a sensor recognition unit 1408 (e.g., or sensor recognition switch). As illustrated in more detail in FIG. 16, The sensor recognition unit 1408 can be configured to determine a type of the wired sensor 1402. The type of sensor (e.g., or information indicative of the type) can be provided to a processing unit 1412, which can determine whether input signals are intentional, whether multiple signals are intended as a single gesture, and/or other information based on the type of the sensor. The sensor recognition unit 1408 can provide the input signal to a filter 1410. The filter 1410 can filter out unintentional signals as described further herein. For example, the filter 1410 can filter (e.g., block, discard, ignore) repetitive signals above or below a frequency. The filter 1410 can filter signals that do not have expected characteristics (e.g., in the time domain or frequency domain). The sensor recognition unit 1408 can also provide input signals to the processing unit 1412. In some implementations, the input signals can be provided to the filter 1410 and/or the processing unit 1410 without passing through the sensor.

The apparatus 1400 can be battery operated and/or receive power from other power sources. The apparatus 1400 can comprise a power management system 1414. The power management system 1414 can be configured to deliver, manage, conserve and/or the like power throughout the apparatus 1400. The apparatus 1400 can comprise a transformer 1416 electrically coupled to the power management system 1414. For example, the transformer 1416 can comprise a direct current transformer configured to transform an alternating current source to a direct current. In an aspect, the apparatus 1400 can comprise a one or more status indicator systems 1418 as described further herein.

As explained further herein, the processing unit 1412 can be configured to manage one or more of the components of the apparatus 1400. The processing unit 1412 can be configured to determine output signals and select output devices to receive output signals. For example, the processing unit 1412 can determine the output signals based on a number of input signals, frequency of input signals, signal characteristics (e.g., amplitude, frequency, voltage, pattern), which sensors the input signals are received from, time in between the input signals, time the input signals are received (e.g., and how such timing corresponds to information indicated and/or shown on a display), and/or the like.

Figure 15:
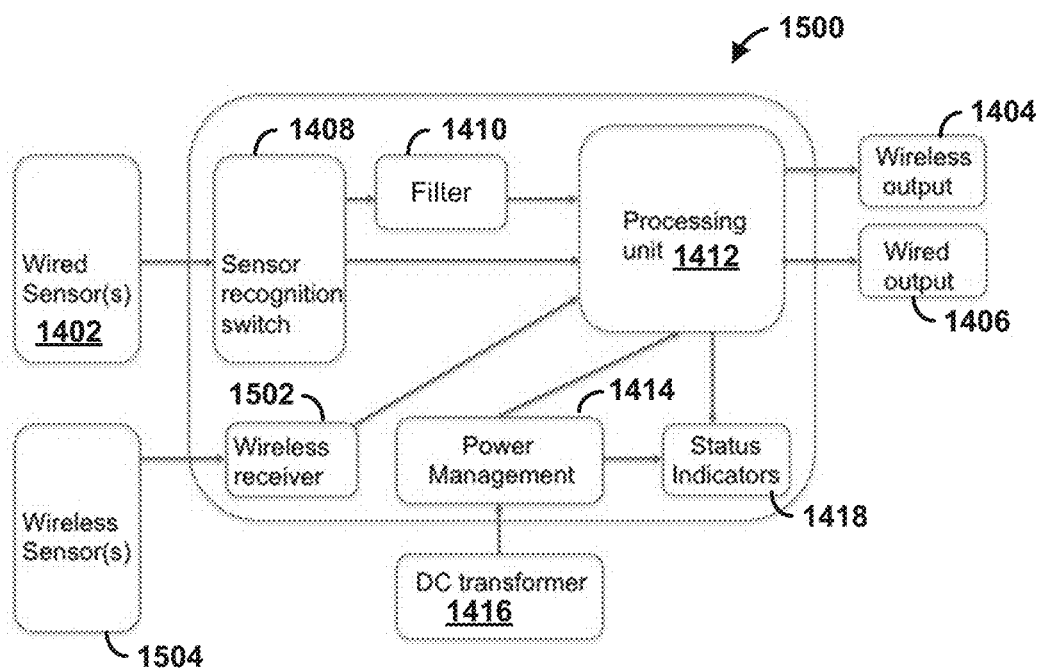
FIG. 15 is a block diagram illustrating another example apparatus.

FIG. 15 is a block diagram illustrating another example apparatus 1500. In an aspect, the apparatus 1500 can comprise one or more of the components of the apparatus 1400 of FIG. 14. The apparatus 1500 can be configured to receive input from one or more wireless sensors. In this implementation, the apparatus 1500 can be configured to accept input from a wireless receiver 1502 communicatively coupled (e.g., paired) with one or more wireless sensors 1504.

In an aspect, the apparatus 1500 can detect an intentional gesture via one of the sensors based on the correct identification of the sensor(s) being used with the apparatus 1500. The apparatus 1500 can receive input from a single sensor or multiple sensors. For example, The apparatus 1500 can receive input (e.g., input signals) from an acoustic microphone (e.g., Noddle-mic™), a proximity/capacitance sensor (e.g., Noddle-touch™), a pressure sensor (e.g., Noddle-bulb™), an IR reflectance sensor (e.g., Noddle-wink™), and/or any other appropriate sensor.

As an illustration, the acoustic microphone can be configured to respond to small intentional tongue clicks that even intubated patients are able to make. The a proximity/capacitance sensor can function as a proximity switch (e.g., responds to a change in capacitance that results by some part of the users body coming in proximity to the sensor) and so can detect small low force movements. The pressure sensor can be activated by compression of a small bulb by the user. The IR reflectance sensor can be activated by an eye blink/wink or by any part of the users body that can alter the IR reflectance beam. Use of a camera and a recognition algorithm to detect head movement or some other gesture can also be used by converting a position change signal into a switch signal.

Figure 16:
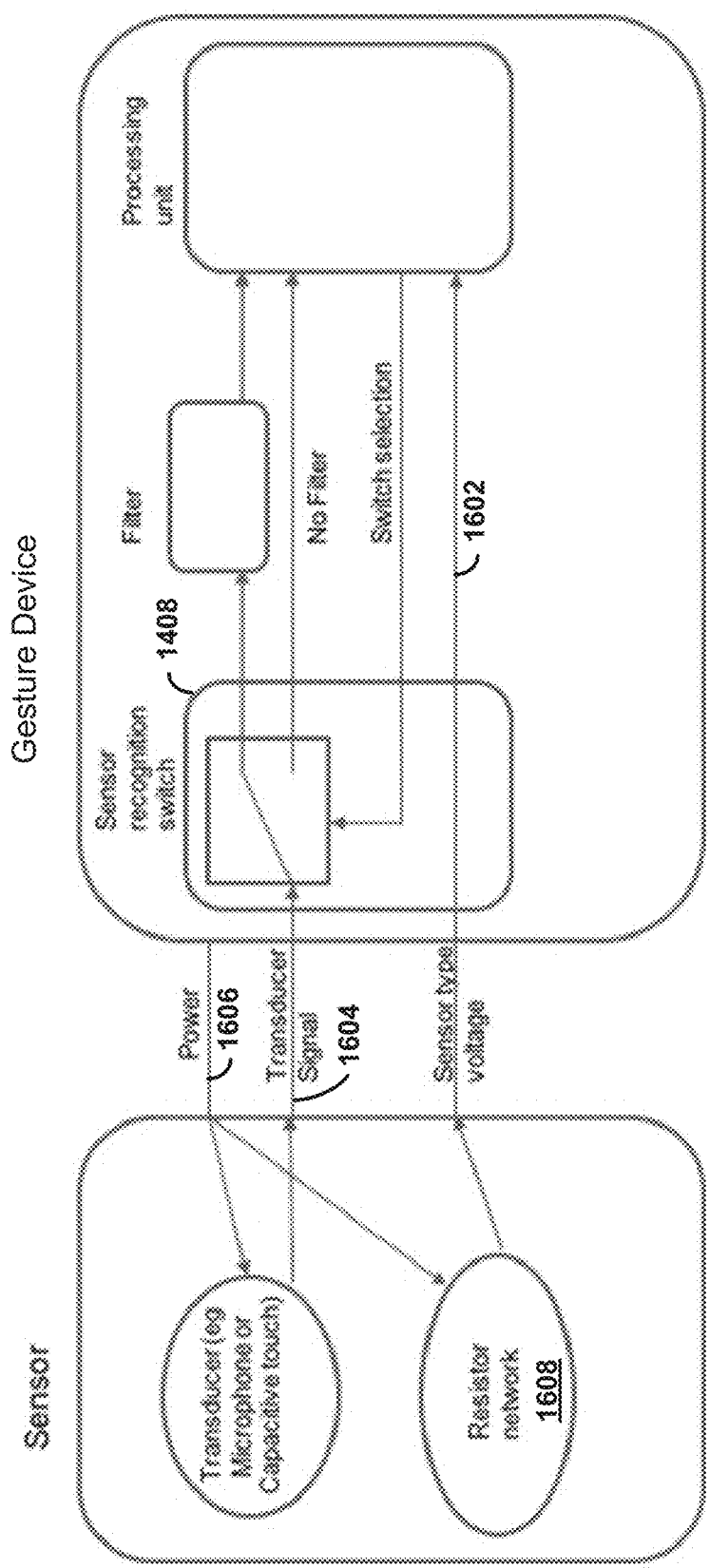
FIG. 16 is a block diagram of an apparatus illustrating aspects of an example sensor recognition switch.

FIG. 16 is a block diagram of an apparatus illustrating aspects of an example sensor recognition switch. In an aspect, the apparatus can be configured to automatically detect the type of sensor being used. As shown in FIG. 16, the apparatus can comprise a sensor recognition switch 1408. The sensor recognition switch 1408 can be configured to recognize a sensor and/or a type of the sensor. The sensor recognition switch 1408 can determine a specific sensor and/or type of sensor (e.g., coupled to the apparatus, providing signals to the apparatus, in range of the apparatus). For example, the sensor recognition switch 1408 can be configured to determine a unique signal voltage produced by a sensor and/or type of sensor. The sensor recognition switch 1408 can determine a resistance value in a parallel input line 1602 that is unique for each sensor. As explained further herein, an additional resistance value (e.g., unique to each sensor, unique to each type of sensor) can be built-in or added to the sensor that would indicate the gesture timing threshold to be used in the gesture detection algorithm.

In an aspect, the sensor recognition switch 1408 can be configured to detect gestures as a function of the user's physical state. For example, a user in a first physical state can make gestures with a first speed, frequency, force, and/or the like. A user in a second physical state can make gestures with a second speed, frequency, force, and/or the like. The sensor recognition switch 1408 can be configured to determine whether gestures are intentional based on which portion of a user is making the gesture, a characteristic (e.g., size, strength, mobility, movement range) of the portion of the user is making the gesture, and/or the like. For example, the sensor recognition switch 1408 can be configured to determine whether a gesture of a limb (e.g., arm, leg) is intentional based on a first force, frequency, speed, and/or the like. The sensor recognition switch 1408 can be configured to determine whether a gesture of an finger, eye, eyelid, and/or the like is intentional based on a second force, frequency, speed, and/or the like.

In an aspect, different types of sensor can be associated with different timing thresholds. For example, the sensors can have fixed characteristics (e.g., voltage, resistance). Thus, the characteristics can be associated with specific timing thresholds. As another example, the sensors can be modified by a user (e.g., via hardware and/or software setting). For example, a sensor can comprise a switch to select different resistance values. Accordingly, the user can set the timing threshold by adjusting the resistance value of the sensor. Where the sensor characteristic is fixed, the user can adjust the timing threshold by using a different sensor or sensor type. In some implementations, an interface of the apparatus can be accessed to adjust which characteristics are associated with which timing thresholds.

In an aspect, the sensor recognition switch 1408 can be configured to determine the type of sensor based on information from the sensor. The information can comprise a code. In the case of wireless sensors, a unique wireless code assigned to a particular type of sensor can be provided by the sensor to the apparatus. The unique code can be used to indicate, determine, and/or the like the gesture timing threshold for a specific sensor. A code can also be provided by wired sensor for identification of the sensor and/or type of sensor.

In an aspect, the sensor recognition switch 1408 can be configured to determine the type of sensor based on hardware and/or software characteristics associated with the sensor. For example, a sensor can be coupled to the apparatus via at least two input lines. A first input line 1604 can provide sensor output from a user. The second input line 1602 can be in parallel with the first input line 1602. The second input line 1602 can comprise a resistor. The apparatus can determine the resistance, voltage drop and/or other characteristic indicative of the sensor based on the first input line 1604 and/or second input line 1602. For example, a signal received from the second input line 1602 can be compared to a power output line 1606 (e.g., of the sensor, a power line from the apparatus to the sensor, a power line of a power source received by the apparatus and/or sensor) to determine the signal (e.g., or information, resistance, value) produced by the resistor network 1608. A voltage difference or other difference in characteristics of the signals from the first input line 1604 and power output line 1606 can be determined to identify the sensor and/or type of sensor.

In another aspect, an input signal sensing algorithm can be used to determine the sensor and/or type of the sensor. For example, sensors and/or types of sensors can be associated with corresponding characteristics, such as signal voltages, signal patterns, signal frequencies, signal waveforms (e.g., sinusoidal, square, triangle), and/or the like.

Figure 17:
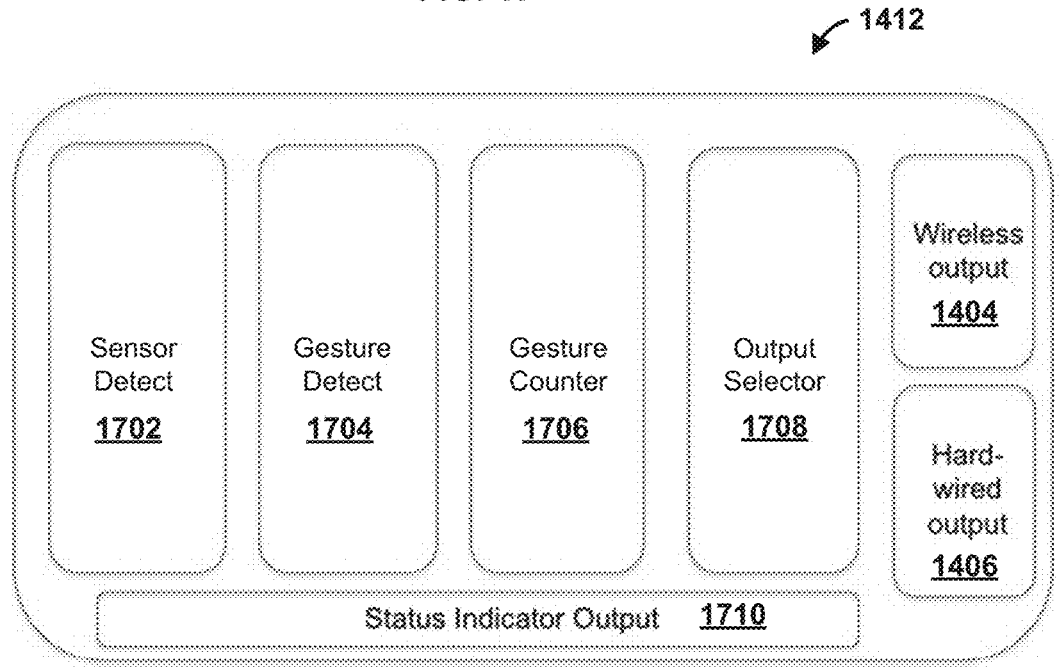
FIG. 17 illustrates an example processing unit of the apparatus.

FIG. 17 illustrates an example processing unit 1412 of the apparatus. The processing unit 1412 can comprise a sensor detection unit 1702. The sensor detection unit 1702 can be configured to detect a sensor and/or type of sensor coupled (e.g., communicatively coupled) to the apparatus. For example, the sensor detection unit 1702 can comprise and/or manage the sensor recognition switch 1408. The processing unit 1412 can comprise a gesture detection unit 1704 configured to classify input signals as intentional or unintentional gestures as explained herein. The processing unit 1412 can comprise a gesture counter unit 1706 configured to count gestures as explained herein. The processing unit 1412 can comprise an output selection unit 1708 configured to select an output based on the number of gestures counted by the gesture counter unit 1706. The output selection unit 1708 can select one or more wireless outputs 1404 and/or wired outputs 1406. The processing unit 1412 can also comprise a status indicator output configured to indicate the status of the processing unit 1412.

When the apparatus is used with a single sensor, the apparatus can allow the user to effectively have the equivalent of at least three switches that can be linked to a range of devices. This is accomplished by the gesture counting algorithm. For example, the first detected gesture can initiate a counting window. The counting window can define an inter-gesture interval (IGI). For an additional gesture to be added to the count a minimal IGI must be exceeded. In addition, if a maximum IGI is exceeded, then the next signal received can be determined as a unique gesture rather than one of a series of related gestures (e.g., or a series of signals related to a signal gesture). An illustration of the gesture counting algorithm using a single sensor is as follows. If the maximum IGI is exceeded without additional detected gesture, then the apparatus will selected (e.g., set, determine) output 1. If a second gesture is detected within the IGI and then the maximum IGI is exceeded without an additional gesture, then the apparatus can selected output 2. If a third gesture is detected within the IGI and then the maximum IGI is exceeded without an additional gesture, then the apparatus can select output 3. If a fourth gesture is detected within the IGI, then the apparatus can determine not to select any output. This last option is included to allow the user to abort if he/she wishes to not have any output set.

Table 1 illustrates an example relationship between the number of counted gestures and the output selected when only a single sensor is used.

TABLE 1

| Number of Gestures | Output Selected |
| --- | --- |
| 1 | 1 |
| 2 | 2 |
| 3 | 3 |
| 4 | (no output) - functions to abort sequence |

Table 2 illustrates the relationship between the number of gestures counted and the output selected when more than one sensor is used. As an illustration, multiple sensors can be used to select outputs as follows. If the maximum IGI is exceeded without additional detected gesture and if the gesture was detected by sensor A, the apparatus can select output 1. If the maximum IGI is exceeded achieved without additional detected gesture and if the gesture was detected by sensor B, the apparatus can select (e.g., determine, set) output 2. If a second gesture is detected from the same sensor (e.g. sensor A) within the IGI and then the maximum IG is exceeded without an additional gesture, then the apparatus can select output 3. If a second gesture is detected from the same sensor (e.g. sensor B) within the IGI and then the maximum IGI is exceeded without an additional gesture, then the apparatus can select output 4. If a second gesture is detected from a different sensor (e.g. sensor A followed by sensor B) within the IGI and then the maximum IGI is exceeded without an additional gesture, then the apparatus can select output 5. If a second gesture is detected from a different sensor (e.g. sensor B followed by sensor A) within the IGI and then the maximum IGI is exceeded without an additional gesture, then the apparatus can select output 6. If three gestures are detected within the IGI, regardless of which sensors are activated, then the apparatus can select no output. Any three gesture sequence allows the user to abort if he/she wishes to not have any output set. It should be understood that the apparatus can be configured to count longer strings of gestures from one or more sensors thereby allowing for control of a larger number of outputs.

TABLE 2

| First Gesture Detected Sensor ID | Second Gesture Detected Sensor ID | Third Gesture Detected Sensor ID | Output Selected |
| --- | --- | --- | --- |
| A | — | — | 1 |
| B | — | — | 2 |
| A | A | — | 3 |
| B | B | — | 4 |
| A | B | — | 5 |
| B | A | — | 6 |
| A | A | A or B | (no output) |
| B | B | A or B | (no output) |
| A | B | A or B | (no output) |
| B | A | A or B | (no output) |

As illustrated in FIG. 14, FIG. 15, and FIG. 17, the apparatus can provide both hardwired and wireless outputs. The hardwired outputs can be isolated relay outputs (e.g., an electrically operated switch). The isolated relay outputs can be configured as either normally open or normally closed. In an aspect, the apparatus can provide output signals comprising commands, characters (e.g., keyboard characters), function parameters, device settings. For example, the output can be in the form of a set (e.g., string, array, formatted data structure) of characters (e.g., keyboard characters). The apparatus also can provide the output via a serial port (e.g., USB port), wireless transceiver, network interface, and/or the like. Example commands can comprise a power on, power off, volume up, volume down, channel up, channel down, pause, play, fast forward, rewind, mute, open application, close application, like command, bookmark command, nurse call command, dial number, temperature setting, temperature up, temperature down, light on, light off, medication request, indicate an increase in pain level, indicate a decrease in pain level, changing feeling status, and/or the like. As another example, the command can comprise any language, speech, text, audio and/or the like generated by a user by issuing commands (e.g., selecting letters, words, or otherwise generating output) to a speech generation device. Through a speech generation device coupled to the apparatus there is almost no limit as to what the patient can communicate depending on how the device is programmed and set up.

In an aspect, the processing unit 1412 can be configured to control the status indicator system 1418 which provides the user feedback about the status of the device hardware, about the detection of intentional gestures, and/or other useful information. For example, the status indicator system 1418 can comprise a power indicator (e.g., LED power indicator). The power indicator can provide a steady illumination (e.g., green light) when the device is on. The status indicator system 1418 can comprise a charging indicator. The charging indicator can provide steady illumination when a battery of the apparatus is charging. The charging indicator can flash to indicate a battery charge error. When the charging indicator is not illuminated, the charge is complete and/or the apparatus is not charging the battery. The status indicator system 1418 can comprise a low battery indicator. The low battery indicator can flash (e.g., flash red) when the battery is low. A noise can also be emitted (e.g., pulsing beep). The status indicator system 1418 can comprise a sensor connection indicator. When a sensor is not coupled to the apparatus, a signal (e.g., red illumination) can be provided by the sensor connection indicator. The status indicator system 1418 can comprise a gesture detection indicator. The gesture detection indicator can provide a number of flashes (e.g., blue flashes) corresponding to a number of detected gestures. The status indicator system 1418 can comprise an output selection indicator. The output selection indicator can provide a number of flashes (e.g., green flashes) indicator a number of the selected output.

Figure 18:
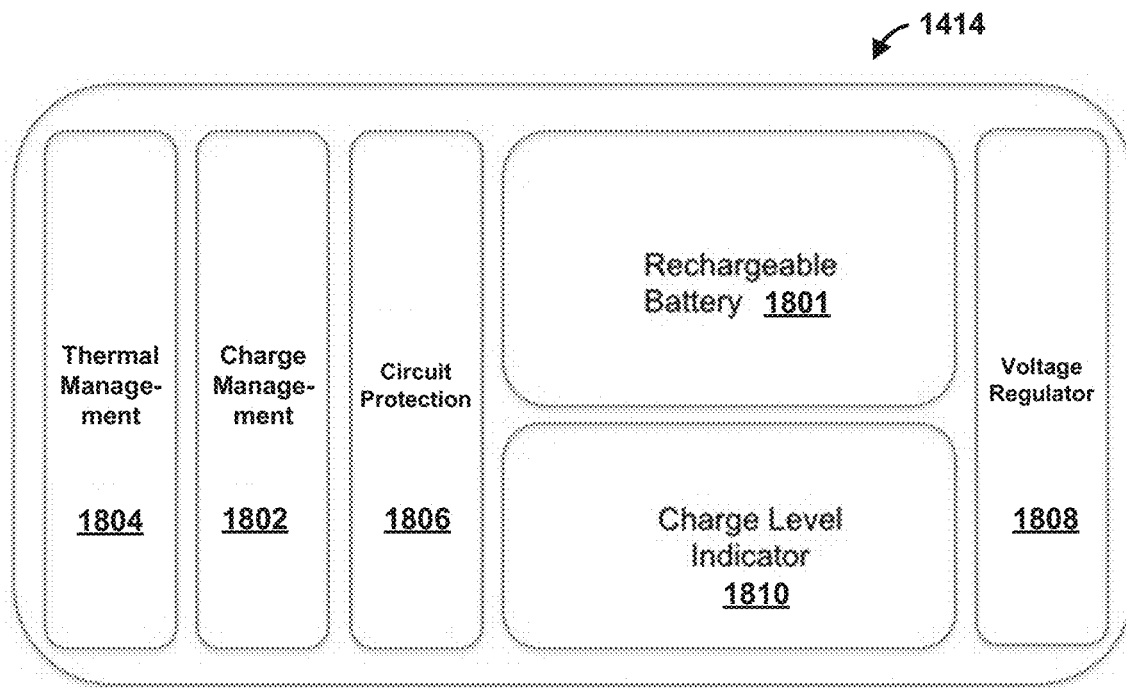
FIG. 18 illustrates an example power management system.

FIG. 18 illustrates an example power management system 1414. The apparatus can be powered from either the electrical mains using a DC power adapter (e.g., DC transformer 1416) or secondarily by an internal rechargeable battery 1801. The power management system 1414 can comprise a charge management system 1802 configured to prevent over charging of the internal battery 1801. The power management system 1414 also can comprise safety features like a thermal cutoff element 1804 to preclude the possibility of overheating and the risks of fire. The power management system 1414 can also comprise a circuit protection element 1806, a voltage regulator 1808, a charge level indicator 1810, and/or other elements related to power management.

Figure 19:
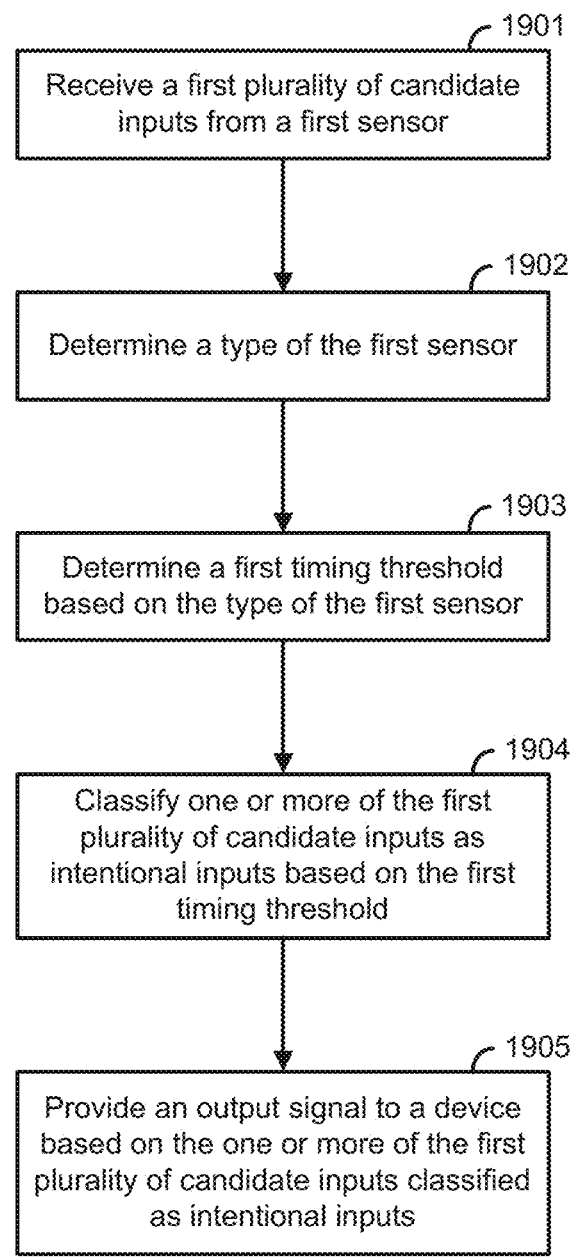
FIG. 19 is a flow chart illustrating an example method for managing a device.

FIG. 19 is a flow chart illustrating an example method 1900 for managing a device. At step 1901, a first plurality of candidate inputs can be received from a first sensor. The first plurality of candidate inputs can comprise input signals. The first plurality of candidate input signals can be received via wired and/or wireless communication links.

At step 1902, a type of the first sensor can be determined. The type of the first sensor can be determined based on a voltage level of a signal received from the first sensor. In another aspect, determining the type of the first sense can comprise determining an electrical resistance value of a connection with the first sensor. The type of the first sensor can be determined based on the electrical resistance value.

At step 1903, a first timing threshold can be determined based on the type of the first sensor. The first timing threshold can comprise a minimum duration of time between intentional inputs. For example, different types of sensors can be associated with different timing thresholds. The timing thresholds can be accessed in a data structure, database, and/or the like.

At step 1904, one or more of the first plurality of candidate inputs can be classified as intentional inputs based on the first timing threshold. For example, a difference in time can be determined between a first time of receiving a first candidate input and a second time of receiving a candidate input prior (e.g., the immediately prior) to the first candidate input. If the difference is less than the first timing threshold, then the first candidate signal can be classified as unintentional. If the difference is greater than the first timing threshold, then the first candidate signal can be classified as intentional.

At step 1905, an output signal can be provided to a device based on the one or more of the first plurality of candidate inputs classified as intentional inputs. The device can be selected based on a number of the first plurality of candidate inputs classified as intentional inputs. For example, step 1905 can comprise counting a number of the one or more of the first plurality of candidate inputs classified as intentional inputs. The device can be selected based on the number.

In another aspect, the method 1900 can further comprise receiving a second plurality of candidate inputs from a second sensor. A type of the second sensor can be determined. A second timing threshold can be determined based on the type of the second sensor. The device can be selected for receiving the output signal based on a combination of a number of the first plurality of inputs classified as intentional inputs and a number of the second plurality of inputs classified as intentional inputs.

Figure 20:
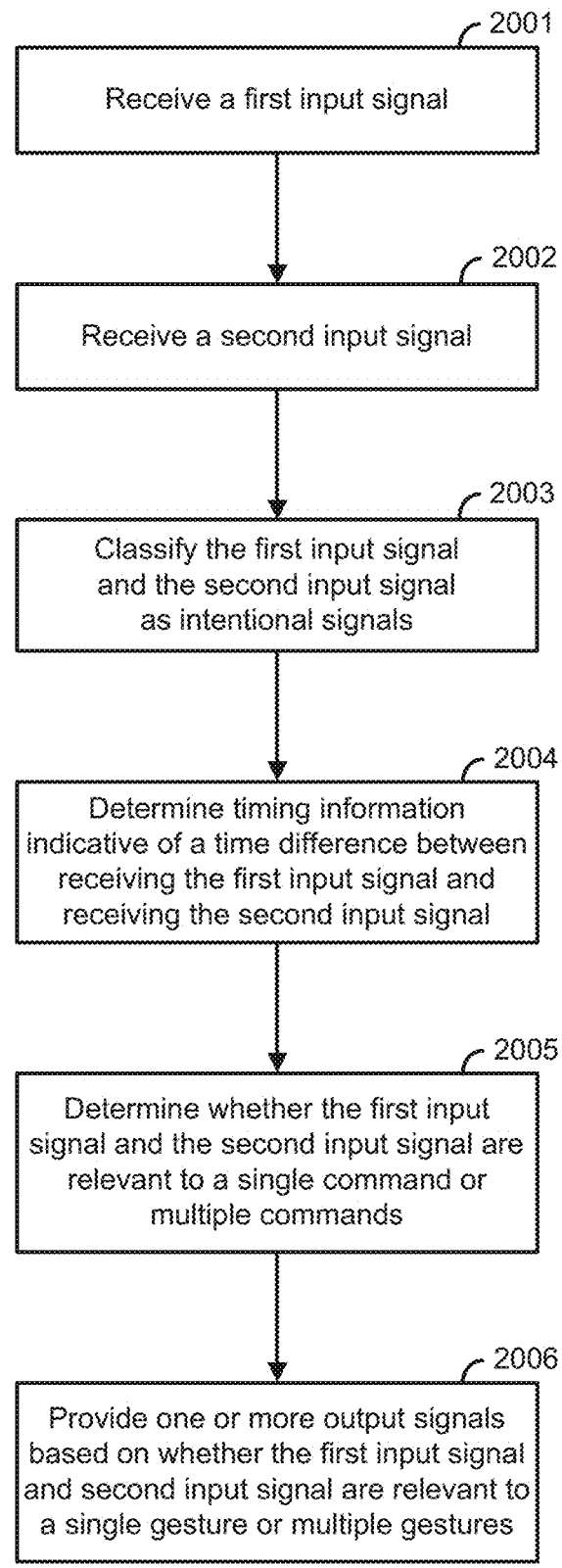
FIG. 20 is a flow chart illustrating an example method for recognizing a gesture.

FIG. 20 is a flow chart illustrating an example method 2000 for recognizing a gesture. At step 2001, a first input signal can be received. The first input signal can be received from a first sensor. The first sensor can comprise touch sensor, a pressure sensor, a mechanical sensor, an optical reflectance sensor, an infrared reflectance sensor, a light sensor, a proximity detector, a capacitance sensor, an audio sensor, and a camera. As a further example, the first sensor can comprise an infrared reflectance sensor, a pressure bulb sensor, a proximity capacitance sensor, an acoustic microphone sensor, and/or any other appropriate sensor. The first sensor can be configured to provide only one type of signal or multiple types of signals (e.g., having variable voltages, frequencies, currents, and/or the like). For example, the first sensor can provide a single type of signal having a set characteristic (e.g., voltage, frequency, amplitude, pattern, and/or the like). In another aspect, the characteristics of the signal can vary based on the force applied by the user to the first sensor and/or other settings that the user can modify.

At step 2002, a second input signal can be received after the first input signal. The second input signal can be received from the first sensor and/or a second sensor. The second sensor can comprise a touch sensor, a pressure sensor, a mechanical sensor, an optical reflectance sensor, an infrared reflectance sensor, a light sensor, a proximity detector, a capacitance sensor, an audio sensor, and a camera. As a further example, the second sensor can comprise an infrared reflectance sensor, a pressure bulb sensor, a proximity capacitance sensor, an acoustic microphone sensor, and/or any other appropriate sensor. The second sensor can be configured to provide only one type of signal or multiple types of signals (e.g., having variable voltages, frequencies, currents, and/or the like). For example, the second sensor can provide a single type of signal having a set characteristic (e.g., voltage, frequency, amplitude, pattern, and/or the like). In another aspect, the characteristics of the second signal can vary based on the force applied by the user to the second sensor and/or other settings that the user can modify. The characteristics of the second signal can be different than the characteristics of the first signal.

At step 2003, the first input signal and/or the second input signal can be classified as intentional signals. For example, the first input signal can be classified based on a first characteristic of the first input signal. The first characteristic can be a time domain characteristic, a frequency domain characteristic, and/or the like. For example, one or more filters (e.g., hi-pass filter, low pass filter) can be applied to the first input signal. The second input signal can be classified based on a second characteristic of the second input signal. The second characteristic can be a time domain characteristic, a frequency domain characteristic, and/or the like. For example, one or more filters (e.g., hi-pass filter, low pass filter) can be applied to the second input signal.

At step 2004, timing information indicative of a time difference between receiving the first input signal and receiving the second input signal can be determined. For example, a first time indicative of the first input signal (e.g., a time when the first input signal is received) can be determined. A second time indicative of the second input signal can be determined (e.g., a time when the second input signal is received). The timing information can comprise a time difference between the first time and the second time (e.g., a length or duration of time between the first time and the second time.

At step 2005, a determination can be made on whether the first input signal and the second input signal are relevant to a single command or multiple commands based on the timing information. For example, step 2005 can comprise comparing the timing information to a gesture time window. The gesture time window can comprise an maximum amount of time before two input signals (e.g., received in succession) are interpreted as relating to different gestures. The gesture time window can be specified by a user providing the first input signal and the second input signal. If the time difference is less than the gesture time window then the first input signal and the second input signal are determined to be relevant to a single gesture. If the time difference is greater than the gesture time window, then the first input signal and the second input signal can be determined to be relevant to two different gestures. In an aspect, the gesture time window can be based on a type of the first sensor and/or a type of the second sensor.

In another aspect, the gesture time window can initiated (e.g., start) in response to receiving the first input signal. The gesture time window can end after a set time. For example, if the end of the gesture time window is after the second time, then the first input signal and the second input signal can be determined to be relevant to the single gesture. If the end of the gesture time window is before the second time, then the first input signal and the second input signal can be determined to be relevant to two separate gestures.

At step 2006, one or more output signals can be provided based on the determination of whether the first input signal and the second input signal are relevant to a single gesture or multiple gestures. For example, the device to provide the one or more output signals to can be selected based on a count of input signals received during the gesture time window.

Figure 21:
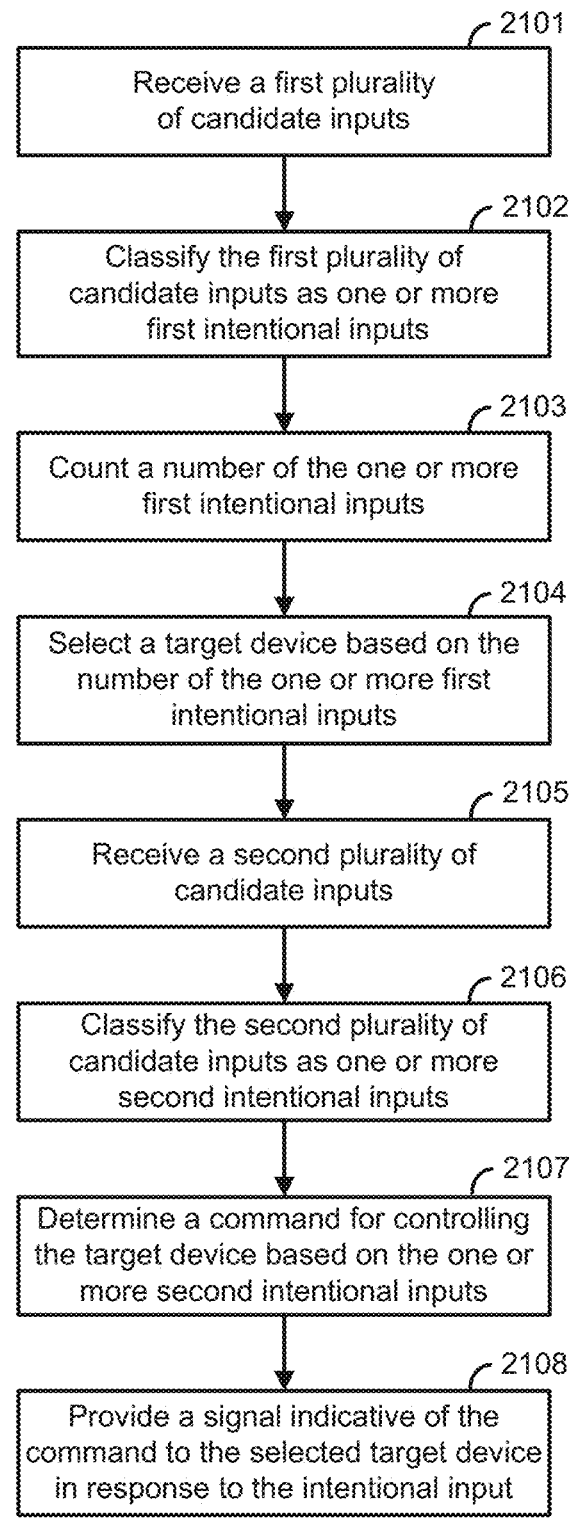
FIG. 21 is a flow chart illustrating an example method for recognizing a gesture.

FIG. 21 is a flow chart illustrating an example method 2100 for recognizing a gesture. At step 2101, a first plurality of candidate inputs can be received. The first plurality of candidate inputs can be received from one or more sensors, via wired and/or wireless communication links. At step 2102, the first plurality of candidate inputs can be classified as one or more first intentional inputs. For example, time domain and/or frequency domain characteristics of the first plurality of candidate inputs can be analyzed to determine which of the first plurality of candidate inputs are intentional as described further herein.

At step 2103, a number of the one or more first intentional inputs can be counted. For example, a hardware or software counter can determine the number. The number can comprise a number counted during a gesture time window. At step 2104, a target device can be selected based on the number of the one or more first intentional inputs. For example, the target device can be associated with the number. Each of a plurality of outputs can be give an a corresponding number.

At step 2105, a second plurality of candidate inputs can be received. For example, after a target device is selected, a command detection time window can begin (e.g., be initiated). During the command detection time window, candidate inputs determined as intentional can be used to determine a command. At step 2106, the second plurality of candidate inputs can be classified as one or more second intentional inputs. For example, time domain and/or frequency domain characteristics of the first plurality of candidate inputs can be analyzed to determine which of the first plurality of candidate inputs are intentional as described further herein.

At step 2107, a command for controlling the target device can be determined based on the one or more second intentional inputs. The command can comprise a command for an application on the target device. For example, the target device can be associated with and/or support a plurality of commands. The command can be determined based on a characteristic (e.g., a number, a pattern, a frequency, a voltage) of the one or more second intentional inputs. For example, the command can be associated with a corresponding number (e.g., or other characteristic) for the target device (e.g., or an application thereon). The number can be specific to the target device. As an illustration, if three intentional inputs are received in the command detection time window, then the command associated with the number three can be provided to the target device.

At step 2108, a signal indicative of the command to the selected target device can be provided in response to the intentional input. The signal can comprise characters indicative of the command, voltages, signals patterns, amplitudes and/or other information for identifying the command.

While the methods and systems have been described in connection with preferred embodiments and specific examples, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

Throughout this application, various publications are referenced. The disclosures of these publications in their entireties are hereby incorporated by reference into this application in order to more fully describe the state of the art to which the methods and systems pertain.

It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

What is claimed is:

1. An apparatus comprising:
one or more processors; and
memory storing processor-executable instructions that, when executed by the one or more processors, cause the apparatus to:
receive a first input signal from a first sensor configured to detect only a single gesture;
receive a second input signal from the first sensor;
classify the first input signal and the second input signal as intentional signals;
determine timing information indicative of a time difference between receiving the first input signal and receiving the second input signal;
determine, based on the timing information, whether the first input signal and the second input signal are relevant to a single command or multiple commands;
select, based on a count of input signals received during a first gesture time window, a device from a plurality of devices to provide one or more output signals to, wherein each device of the plurality of devices is associated with a respective number and a number of the device matches the count of the input signals; and
send, to the device, the one or more output signals based on determining whether the first input signal and the second input signal are relevant to the single command or the multiple commands.

2. The apparatus of claim 1, wherein the processor-executable instructions that cause the apparatus to determine whether the first input signal and the second input signal are relevant to the single command or the multiple commands comprise processor-executable instructions that, when executed by the one or more processors, cause the apparatus to:
compare the timing information to a second gesture time window,
wherein the apparatus determines that the first input signal and the second input signal are relevant to a gesture if the time difference is less than the second gesture time window.

3. The apparatus of claim 2, wherein the first gesture time window is defined by the first input signal and the second input signal.

4. The apparatus of claim 1, wherein the apparatus receives the second input signal received from a second sensor.

5. An apparatus comprising:
one or more processors; and
memory storing processor-executable instructions that, when executed by the one or more processors, cause the apparatus to:
receive a plurality of candidate inputs from a first sensor configured to detect only a single gesture;
classify the plurality of candidate inputs as one or more intentional inputs;
count a number of the one or more intentional inputs;
select a target device of a plurality of devices based on the number of the one or more intentional inputs, wherein each device of the plurality of devices is associated with a respective number and a number of the target device matches the number of the one or more intentional inputs; and
send a signal to the selected target device in response to the classified one or more intentional inputs.

6. The apparatus of claim 5, wherein the processor-executable instructions that cause the apparatus to receive the plurality of candidate inputs comprise processor-executable instructions that, when executed by the one or more processors, cause the apparatus to receive an input from a second sensor.

7. The apparatus of claim 5, wherein the first sensor comprises one or more of a touch sensor, a pressure sensor, a mechanical sensor, an optical reflectance sensor, an infrared reflectance sensor, a light sensor, a proximity detector, a capacitance sensor, an audio sensor, or a camera.

8. The apparatus of claim 5, wherein the processor-executable instructions that cause the apparatus to classify the plurality of candidate inputs as the one or more intentional inputs comprise processor-executable instructions that, when executed by the one or more processors, cause the apparatus to:
determine a characteristic of an intentional input;
generate a filter based on the characteristic; and
apply the filter to one or more of the plurality of candidate inputs.

9. The apparatus of claim 8, wherein the processor-executable instructions, when executed by the one or more processors, further cause the apparatus to derive the characteristic from a frequency domain.

10. The apparatus of claim 8, wherein the processor-executable instructions, when executed by the one or more processors, further cause the apparatus to derive the characteristic from a time domain.

11. The apparatus of claim 5, wherein the processor-executable instructions that cause the apparatus to send the signal to the selected target device comprise processor-executable instructions that, when executed by the one or more processors, cause the apparatus to activate one or more of a nurse call switch, a computer, a television; a fan, a light, a telephone, or a medical device.

12. The apparatus of claim 5, wherein the processor-executable instructions that cause the apparatus to send the signal to the selected target device comprise processor-executable instructions that, when executed by the one or more processors, cause the apparatus to control the selected target device.

13. An apparatus comprising:
one or more processors; and
memory storing processor-executable instructions that, when executed by the one or more processors, cause the apparatus to:
receive a first plurality of candidate inputs from a first sensor configured to detect only a single gesture;
determine a type of the first sensor;
determine a first timing threshold based on the type of the first sensor;
classify one or more of the first plurality of candidate inputs as intentional inputs based on the first timing threshold; and
send an output signal to a device of a plurality of devices based on the one or more of the first plurality of candidate inputs classified as intentional inputs, wherein each device of the plurality of devices is associated with a respective number and a number of the device matches a number of the first plurality of candidate inputs classified as intentional inputs.

14. The apparatus of claim 13, wherein the processor-executable instructions, when executed by the one or more processors, cause the apparatus to determine the type of the first sensor based on a voltage level of a signal received from the first sensor.

15. The apparatus of claim 13, wherein the processor-executable instructions, when executed by the one or more processors, cause the apparatus to determine the type of the first sensor based on a code received from the first sensor.

16. The apparatus of claim 13, wherein the processor-executable instructions, when executed by the one or more processors, further cause the apparatus to determine an electrical resistance value of a connection with the first sensor, wherein the type of the first sensor is determined based on the electrical resistance value.

17. The apparatus of claim 13, wherein the first timing threshold comprises a minimum duration of time between intentional inputs.

18. The apparatus of claim 13, wherein the processor-executable instructions that cause the apparatus to send the output signal to the device comprise processor-executable instructions that, when executed by the one or more processors, cause the apparatus to:
count a number of the one or more of the first plurality of candidate inputs classified as intentional inputs; and
select the device based on the number.

19. The apparatus of claim 13, wherein the processor-executable instructions, when executed by the one or more processors, further cause the apparatus to:
receive a second plurality of candidate inputs from a second sensor;
determine a type of the second sensor; and
determine a second timing threshold based on the type of the second sensor,
wherein the device to send the output signal to is selected based on a combination of a number of the first plurality of candidate inputs classified as intentional inputs and a number of the second plurality of candidate inputs classified as intentional inputs.

20. The apparatus of claim 13, further comprising:
an input interface configured to receive the first plurality of candidate inputs; and
an output interface configured to send the output signal.

* * * * *